(12) United States Patent
Kirchhofer et al.

(10) Patent No.: US 7,432,044 B2
(45) Date of Patent: Oct. 7, 2008

(54) METHODS AND COMPOSITIONS FOR MODULATING HEPATOCYTE GROWTH FACTOR ACTIVATION

(75) Inventors: Daniel K. Kirchhofer, Los Altos, CA (US); Paul M. Moran, El Cerrito, CA (US); Mark D. Peek, Granite Bay, CA (US)

(73) Assignee: Genentech, Inc., South San Francisco, CA (US)

( * ) Notice: Subject to any disclaimer, the term of this patent is extended or adjusted under 35 U.S.C. 154(b) by 175 days.

(21) Appl. No.: 11/189,230

(22) Filed: Jul. 25, 2005

(65) Prior Publication Data

US 2006/0084120 A1    Apr. 20, 2006

Related U.S. Application Data

(60) Provisional application No. 60/591,339, filed on Jul. 26, 2004.

(51) Int. Cl.
*C12Q 1/00* (2006.01)
*C12Q 1/37* (2006.01)

(52) U.S. Cl. .................... 435/4; 435/338; 435/7.4; 435/23

(58) Field of Classification Search ................. None
See application file for complete search history.

(56) References Cited

U.S. PATENT DOCUMENTS

| | | | |
|---|---|---|---|
| 5,981,830 | A | 11/1999 | Wu et al. |
| 6,423,543 | B1 | 7/2002 | Marcotte et al. |
| 6,482,630 | B2 | 11/2002 | Gan et al. |
| 2003/0013097 | A1 | 1/2003 | Welsh et al. |
| 2003/0049645 | A1 | 3/2003 | Mu et al. |
| 2003/0175736 | A1 | 9/2003 | Chinnaiyan et al. |
| 2003/0223973 | A1 | 12/2003 | O'Brien et al. |
| 2004/0001801 | A1 | 1/2004 | Madison et al. |
| 2004/0009911 | A1 | 1/2004 | Harris et al. |
| 2004/0132156 | A1 | 7/2004 | Parry et al. |

FOREIGN PATENT DOCUMENTS

| WO | WO 02/059373 A2 | 8/2002 |
|---|---|---|
| WO | WO 02/064839 A2 | 8/2002 |
| WO | WO 2004/009803 | 1/2004 |

OTHER PUBLICATIONS

Wells, 1990, Biochemistry 29:8509-8517.*
Ngo et al., 1994, The Protein Folding Problem and Tertiary Structure Prediction, pp. 492-495.*
Birchmeier et al., "Met, Metastasis, Motility and More" *Nature Reviews Molecular Cell Biology* 4 :915-925 (2003).
Carmeliet et al., "Physiological consequences of loss of plasminogen activator gene function in mice" *Nature* 368(6470) :419-424 (1994).
Delaria et al., "Characterization of placental bikunin, a novel human serine protease inhibitor" *J Biol Chem.* 272(18) :12209-12214 (May 2, 1997).

Denda et al., "Functional characterization of Kunitz domains in hepatocyte growth factor activator inhibitor type 1" *J Biol Chem.* 277(16) :14053-14059 (Apr. 19, 2002).
Dennis and Lazarus, "Kunitz Domain Inhibitors of Tissue Factor-Factor VIIa; I. Potent Inhibitors Selected from Libraries by Phage Display" *Journal of Biological Chemistry* 269(35) :22129-22136 (1994).
Dennis et al., "Potent and selective Kunitz domain inhibitors of plasma kallikrein designed by phage display" *J Biol Chem.* 270(43) :25411-25417 (Oct. 27, 1995).
Dhanasekaran et al., "Delineation of prognostic biomarkers in prostate cancer" *Nature* 412(6849) :822-826 (Aug. 23, 2001).
Gailani et al., "A murine model of factor XI deficiency" *Blood Coag. Fibrinol.* 8 :134-144 (1997).
Gak et al., "Processing of Hepatocyte Growth Factor to the Heterodimeric Form is Required for Biological Activity" *FEBS Letters* 311(1) :17-21 (1992).
Gmyrek et al., "Normal and malignant prostate epithelial cells differ in their response to hepatocyte growth factor/scatter factor" *Am J Pathol.* 159(2) :579-590 (Aug. 2001).
Hamasuna et al., "Reduced expression of hepatocyte growth factor activator inhibitor type-2/placental bikunin (HAI-2/PB) in human glioblastomas: implication for anti-invasive role of HAI-2/PB in glioblastoma cells" Int J Cancer 93:339-3435 (2001).
Hartmann et al., "A Functional Domain in the Heavy Chain of Scatter Factor/Hepatocyte Growth Factor Binds the c-Met Receptor and Induces Cell Dissociation but Not Mitogenesis" *Proc. Natl. Acad. Sci. USA* 89:11574-11578 (Dec. 1992).
Hathaway et al., "Clinical and physiologic studies of two siblings with prekallikrein (Fletcher factor) deficiency" *Am J Med.* 60(5) : 654-664 (May 10, 1976).
Herter et al., "Hepatocyte growth factor is a preferred in vitro substrate for human hepsin, a membrane-anchored serine protease implicated in prostate and ovarian cancers" *Biochemical Journal* 390:124-136 (Apr. 20, 2005).
Huntsman et al., "Comparisin of c-met expression in ovarian epithelial tumors and normal epithelia of the female reproductive tract by quantitative laser scan microscopy" *Am J Pathol.* 155(2) : 1318-1328 (Aug. 199).
Husten et al., "The active site of blood coagulation factor Xa. Its distance from the phospholipid surface and its conformational sensitivity to components of the prothrombinase complex" *J Biol Chem.* 262(27) :12953-12961 (Sep. 25, 1987).
Kataoka et al., "Activation of Hepatocyte Growth Factor/Scatter Factor in Colorectal Carcinoma" *Cancer Research* 60:6148-6159 (2000).

(Continued)

*Primary Examiner*—Elizabeth C. Kemmerer
*Assistant Examiner*—Christina Borgeest
(74) *Attorney, Agent, or Firm*—Cara M. Coburn

(57) ABSTRACT

The invention provides methods and compositions for modulating hepsin activity and the HGF/c-met signaling pathway, in particular by regulating pro-HGF activation by hepsin.

4 Claims, 9 Drawing Sheets

OTHER PUBLICATIONS

Kataoka et al., "Conserved expression of hepatocyte Conserved expression of hepatocyte growth factor activator inhibitor type-2/placental bikunin in human colorectal carcinomas" *Cancer Lett.* 148(2) :127 (Feb. 1, 2000).

Kataoka et al., "Distribution of hepatocyte growth factor activator inhibitor type 1 (HAI-1) in human tissues. Cellular surface localization of HAI-1 in simple columnar epithelium and its modulated expression in injured and regenerative tissues" *J Histochem Cytochem.* 47(5) :673-682 (May 1999).

Kataoka et al., "Evaluation of hepatocyte growth factor activator inhibitor expression in normal and malignant colonic mucosa" *Cancer Lett.* 128(2) :219-227 (Jun. 19, 1998).

Kawaguchi et al., "Purification and cloning of hepatocyte growth factor activator inhibitor type 2, a Kunitz-type serine protease inhibitor" *J Biol Chem.* 272(44) :27558-27564 (Oct. 31, 1997).

Kazama et al., "Hepsin, a putative membrane-associated serine protease, activates human factor VII and initiates a pathway of blood coagulation on the cell surface leading to thrombin formation" *J Biol Chem.* 270(1) :66-72 (Jan. 6, 1995).

Kelley et al., "Similar molecular interactions of factor VII and factor VIIa with the tissue factor region that allosterically regulates enzyme activity" *Biochemistry* 43(5) :1223-1229 (Feb. 10, 2004).

Kirchhofer et al., "Hepsin activates pro-hepatocyte growth factor and is inhibited by hepatocyte growth factor activator inhibitor-1B (HAI-1B) and HAI-2" *FEBS Letters* 579(9) :1945-1950 (Mar. 28, 2005).

Kirchhofer et al., "Structural and Functional Basis of the Serine Protease-like Hepatocyte Growth Factor β-Chain in Met Binding and Signaling" *Journal of Biological Chemistry* 279:39915-39924 (2004).

Kirchhofer et al., "Tissue expression, protease specificity, and Kunitz domain functions of hepatocyte growth factor activator inhibitor-1B (HAI-1B), a new splice variant of HAI-1" *J Biol Chem.* 278(38) : 36341-36349 (Sep. 19, 2003).

Knudsen et al., "High expression of the Met receptor in prostate cancer metastasis to bone" *Urology* 60(6) :113-117 (Dec. 2002).

Lee et al., "Activation of Hepatocyte Growth Factor and Urokinase/Plasmingoen Activator by Matriptase, an Epithelial Membrane Serine Protease" *Journal of Biological Chemistry* 275:36720-36725 (2000).

Leytus et al., "A novel trypsin-like serine protease (hepsin) with a putative transmembrane domain expressed by human liver and hepatoma cells" *Biochemistry* 27(3) :1067-1074 (Feb. 9, 1988).

Lin et al., "Molecular cloning of cDNA for matriptase, a matrix-degrading serine protease with trypsin-like activity" *J Biol Chem.* 274(26) :18231-18236 (Jun. 25, 1999).

Lin et al., "Purification and characterization of a complex containing matriptase and a kunitz-type serine protease inhibitor from human milk" *J Biol Chem* 272(26) :18237-18242 (1999).

List et al., "Matriptase/MT-SP1 is required for postnatal survival, epidermal barrier function, hair follicle development, and thymic homeostasis" *Oncogene* 21(23) :3765-3779 (May 23, 2002).

Lokker et al., "Structure-Function Analysis of Hepatocyte Growth Factor: Identification of Variants that Lack Mitogenic Activity Yet Retain High Affinity Receptor Binding" *EMBO Journal* 11(7) :2503-2510 (1992).

Luo et al., "Human prostate cancer and benign prostatic hyperplasia: molecular dissection by gene expression profiling" *Cancer Research* 61(12) :4683-4688 (Jun. 15, 2001).

Magee et al., "Expression profiling reveals hepsin overexpression in prostate cancer" *Cancer Research* 61(15) :5692-5696 (Aug. 1, 2001).

Mann, K.G., "Biochemistry and Physiology of Blood Coagulation" *Thrombosis and Haemostasis* 82:165-174 (1999).

Marlor et al., "Identification and cloning of human placental bikunin, a novel serine protease inhibitor containing two Kunitz domains" *J Biol Chem.* 272(18) :12202-12208 (May 2, 1997).

McCallum et al., "The location of the active site of blood coagulation factor VIIa above the membrane surface and its reorientation upon association with tissue factor. A fluorescence energy transfer study" *J Biol Chem.* 271(45) :28168-28175 (Nov. 8, 1996).

Mimms et al., "Phospholipid Vesicle Formation and Transmembrane Protein Incorporation Using Octyl Glucoside" *Biochemistry* 20(4) : 833-840 (1981).

Miyazawa et al., "Molecular Cloning and Sequence Analysis of the cDNA for a Human Serine Protease Responsible for Activation of Hepatocyte Growth Factor" *Journal of Biological Chemistry* 268:10024-10028 (1993).

Mutucumarana et al., "The active site of factor IXa is located far above the membrane surface and its conformation is altered upon association with factor VIIIa. A fluorescence study" *J Biol Chem.* 267(24) :17012-17021 (Aug. 25, 1992).

Naka et al., "Activation of Hepatocyte Growth Factor by Proteolytic Conversion of a Single Chain Form to a Heterodimer" *The Journal of Biological Chemistry* 267(28) :20114-20119 (Oct. 5, 1992).

Naldini et al., "Extracellular Proteolytic Cleavage by Urokinase is Required for Activation of Hepatocyte Growth Factor/Scatter Factor" *EMBO Journal* 11(13) :4825-4833 (1992).

Oberst et al., "Expression of the serine protease matriptase and its inhibitor HAI-1 in epithelial ovarian cancer: correlation with clinical outcome and tumor clinicopathological parameters" *Clin Cancer Res.* 8(4) :1101-1107 (Apr. 2002).

Oberst et al., "Matriptase and HAI-1 are expressed by normal and malignant epithelial cells in vitro and in vivo" *Am J Pathol.* 158(4) : 1301-1311 (Apr. 2001).

Okigaki et al., "Functional Characterization of Human Hepatocyte Growth Factor Mutants Obtained by Deletion of Structural Domains" *Biochemistry* 31(40) :9555-9561 (1992).

Parr et al., "Expression of hepatocyte growth factor/scatter factor, its activator, inhibitors and the c-Met receptor in human cancer cells" *Int J Oncol.* 19(4) :857-863 (Oct. 2001).

Peek et al., "Unusual Proteolytic Activation of Pro-hepatocyte Growth Factor by Plasma Kallikrein and Coagulation Factor XIa" *Journal of Biological Chemistry* 277(49) :47804-47809 (Dec. 6, 2002).

Qin et al., "Functional characterization of Kunitz domains in hepatocyte growth factor activator inhibitor type 2" *FEBS Letters* 436(1) :111-114 (Sep. 25, 1998).

Rapaport and Rao, "The Tissue Factor Pathway: How It Has Become a "Prima Ballerina"" *Thrombosis and Haemostasis* 74 :7-17 (1995).

Schmidt et al., "Scatter factor/hepatocyte growth factor is essential for liver development" *Nature* 373:699-702 (Feb. 23, 1995).

Shimomura et al., "Activation of hepatocyte growth factor by two homologous proteases, blood-coagulation factor XIIa and hepatocyte growth factor activator" *European Journal of Biochemistry* 229:257-261 (1995).

Shimomura et al., "Hepatocyte Growth Factor Activator Inhibitor, a Novel Kunitz-type Serine Protease Inhibitor" *Journal of Biological Chemistry* 272:6370-6376 (1997).

Somoza et al., "The structure of the extracellular region of human hepsin reveals a serine protease domain and a novel scavenger receptor cysteine-rich (SRCR) domain" *Structure* 11(9) :1123-1131 (Sep. 2003).

Srikantan et al., "Hepsin inhibits cell growth/invasion in prostate cancer cells" *Cancer Research* 62(23) :6812-6816 (Dec. 1, 2002).

Stamey et al., "Molecular genetic profiling of Gleason grade 4/5 prostate cancers compared to benign prostatic hyperplasia" *J Urol.* 166(6) :2171-2177 (Dec. 2001).

Stamos et al., "Crystal structure of the HGF beta-chain in complex with the Sema domain of the Met receptor" *EMBO Journal* 23(12) : 2325-2335 (Jun. 16, 2004).

Stephan et al., "Hepsin is highly over expressed in and a new candidate for a prognostic indicator in prostate cancer" *J Urol.* 171(1) : 187-191 (Jan. 17, 2004).

Szabo et al., "Type II transmembrane serine proteases" *Thromb Haemost.* 90(2) :185-193 (Aug. 2003).

Takeuchi et al., "Reverse biochemsitry: Use of macromolecular protease inhibitors to dissect complex biological processes and identify a membrane-type serine protease in epithelial cancer and normal tissue" *Proc. Natl. Acad. Aci. USA* 96:11054-11061 (1999).

Tanimoto et al., "Hepsin, a cell surface serine protease identified in hepatoma cells, is overexpressed in ovarian cancer" *Cancer Research* 57(14) :2884-2887 (Jul. 15, 1997).

Torres-Rosado et al., "Hepsin, a putative cell-surface serine protease, is required for mammalian cell growth" *Proc Natl Acad Sci U S A*. 90(15):7181-7185 (Aug. 1, 1993).

Trusolino et al., "Scatter-factor and semaphorin receptors: cell signalling for invasive growth" *Nat Rev Cancer* 2(4):289-300 (Apr. 2, 2002).

Tsuji et al., "Hepsin, a cell membrane-associated protease. Characterization, tissue distribution, and gene localization" *J Biol Chem*. 266(25):16948-16953 (Sep. 5, 1991).

Uehara et al., "Placental defect and embryonic lethality in mice lacking hepatocyte growth factor/scatter factor" *Nature* 373:702-705 (Feb. 23, 1995).

Vu et al., "Identification and cloning of the membrane-associated serine protease, hepsin, from mouse preimplantation embryos" *J Biol Chem*. 272(50):31315-31320 (Dec. 12, 1997).

Welsh et al., "Analysis of gene expression identifies candidate markers and pharmacological targets in prostate cancer" *Cancer Research* 61(16):5974-5978 (Aug. 15, 2001).

Wong et al., "Coexpression of hepatocyte growth factor-Met: an early step in ovarian carcinogenesis?" *Oncogene* 20(11):1318-1328 (Mar. 15, 2001).

Wu et al., "Generation and characterization of mice deficient in hepsin, a hepatic transmembrane serine protease" *J Clin Invest*. 101(2):321-326 (Jan. 15, 1998).

Yamauchi et al., "Hepatocyte growth factor activator inhibitor types 1 and 2 are expressed by tubular epithelium in kidney and down-regulated in renal cell carcinoma" *J Urol*. 171(2 Pt 1):890-896 (Feb. 2004).

Yu et al., "Mice deficient in hepsin, a serine protease, exhibit normal embryogenesis and unchanged hepatocyte regeneration ability" *Thromb Haemost*. 84(5):865-870 (Nov. 2000).

Zacharski et al., "Expression of the factor VII activating protease, hepsin, in situ in renal cell carcinoma" *Thromb Haemost*. 79(4):876-877 (Apr. 1998).

Zhu et al., "Overexpression and regulation of expression of scatter factor/hepatocyte growth factor in prostatic carcinoma" *Urology* 56(6):1071-1074 (Dec. 20, 2000).

Zhukov et al., "Purification and characterization of hepsin from rat liver microsomes" *Biochim Biophys Acta*. 1337(1):85-89 (Jan. 4, 1997).

* cited by examiner

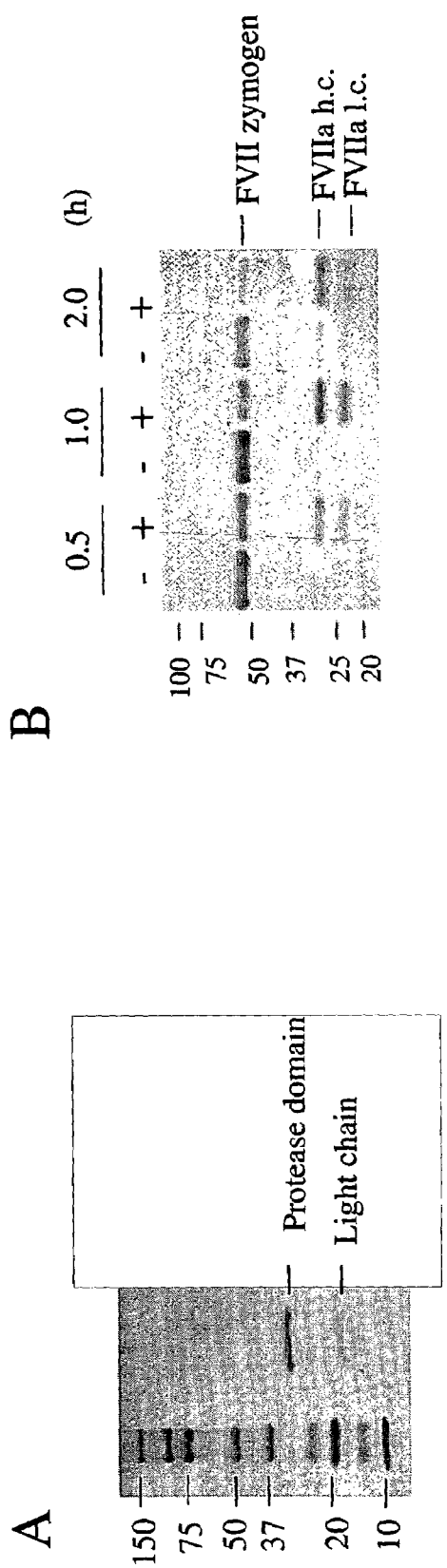
FIG._1

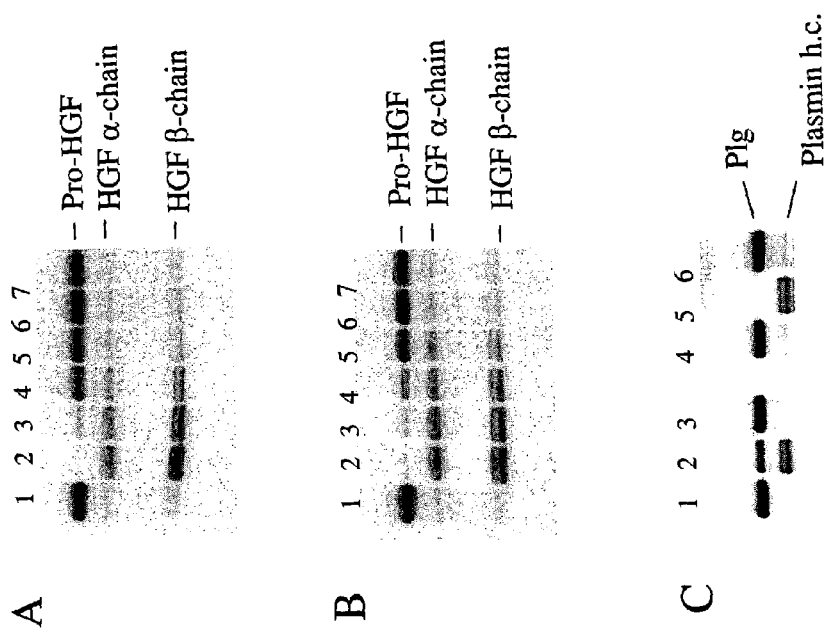
Fig._2

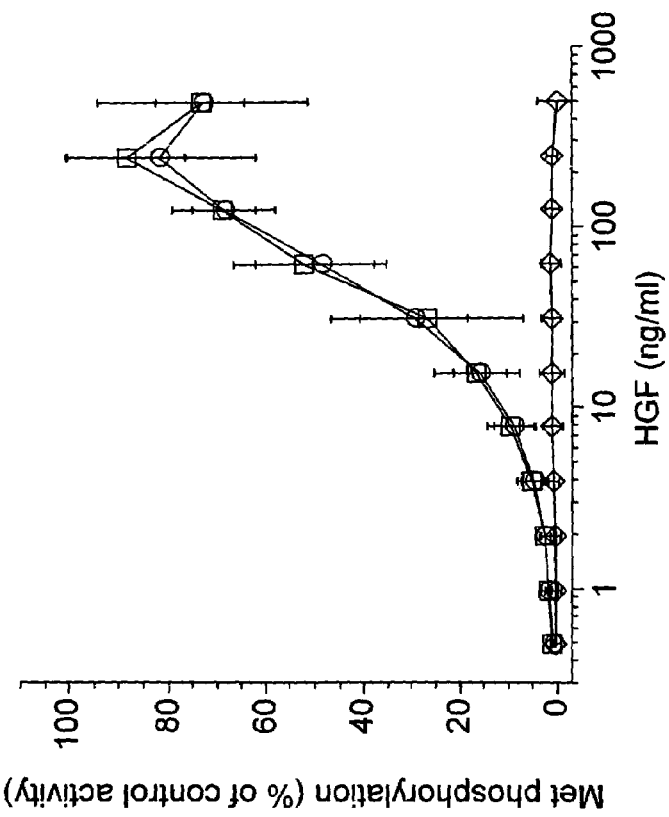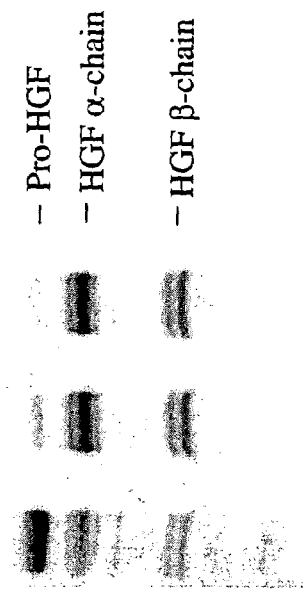
FIG._3

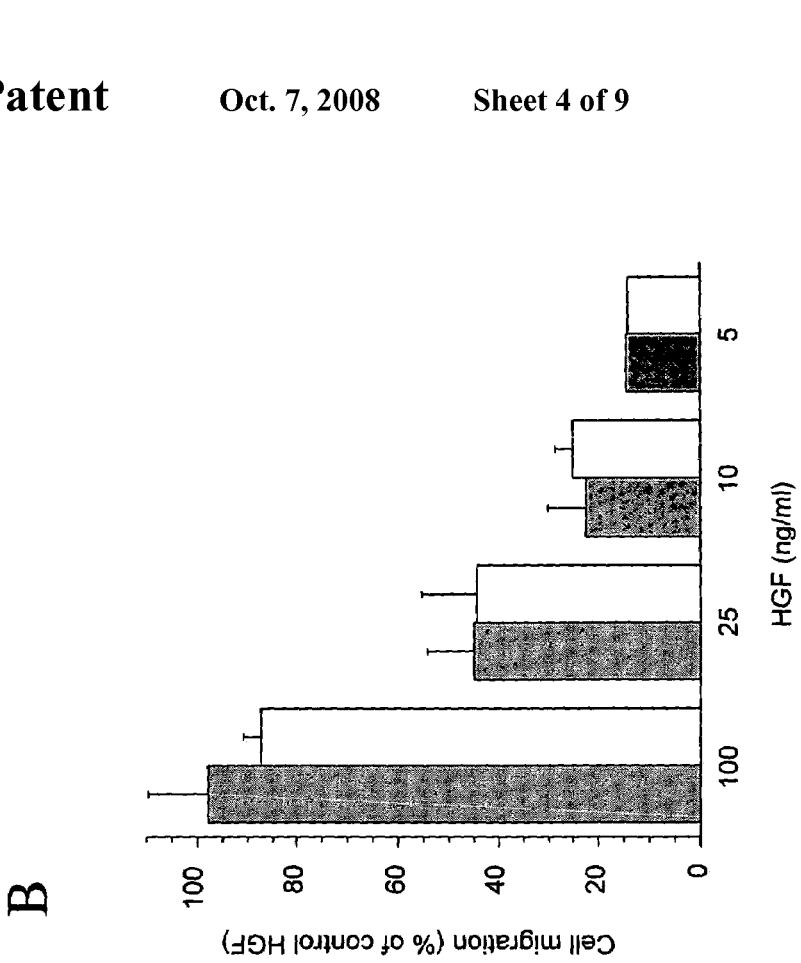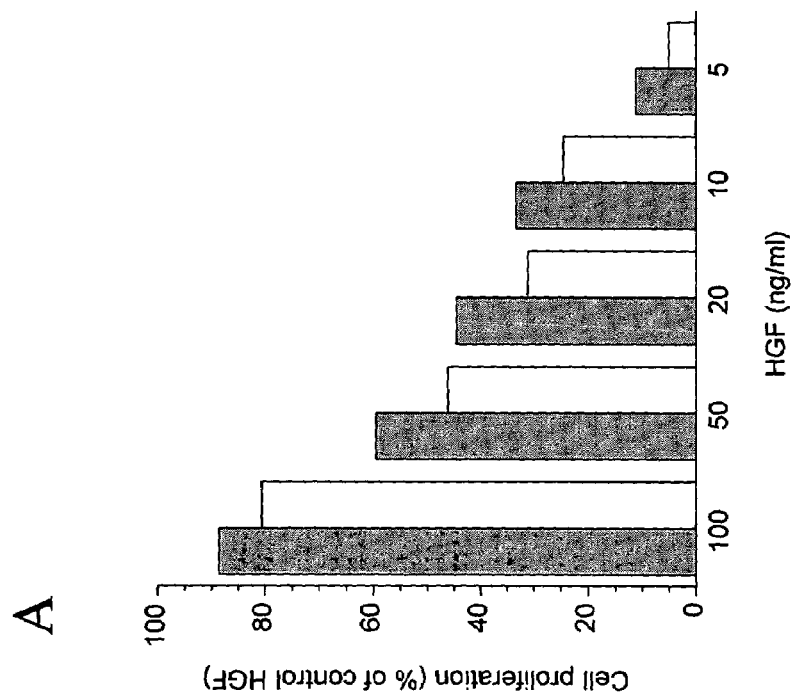
FIG. 4

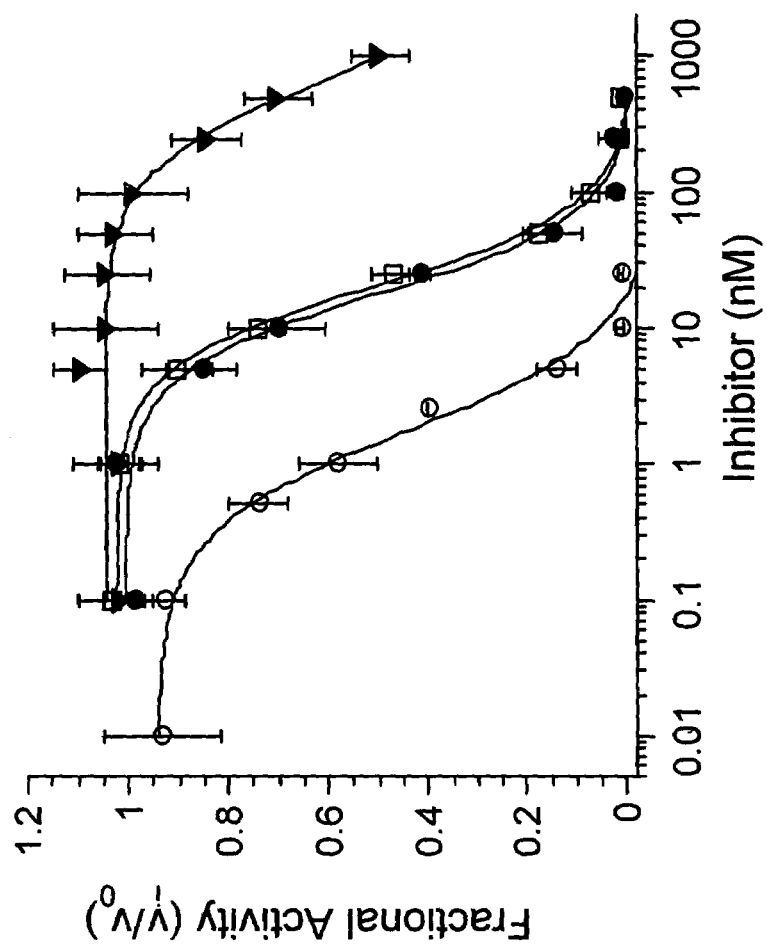
FIG._5

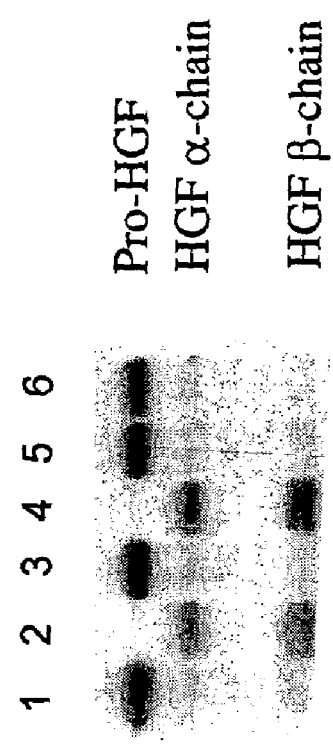
FIG._6

MAQKEGGRTVPCCSRPKVAALTAGTLLLLTAIGAASWAIVAVLLRSDQEPLYPVQVSSAD
ARLMVFDKTEGTWRLLCSSRSNARVAGLSCEEMGFLRALTHSELDVRTAGANGTSGFFCV
DEGRLPHTQRLLEVISVCDCPRGRFLAAICQDCGRRKLPVDRIVGGRDTSLGRWPWQVSL
RYDGAHLCGGSLLSGDWVLTAAHCFPERNRVLSRWRVFAGAVAQASPHGLQLGVQAVVYH
GGYLPFRDPNSEENSNDIALVHLSSPLPTEYIQPVCLPAAGQALVDGKICTVTGWGNTQ
YYGQQAGVLQEARVPIISNDVCNGADFYGNQIKPKMFCAGYPEGGIDACQGDSGGPFVCE
DSISRTPRWRLCGIVSWGTGCALAQKPGVYTKVSDFREWIFQAIKTHSEASGMVTQL (SEQ ID NO:1)

```
Met Ala Gln Lys Glu Gly Gly Arg Thr Val Pro Cys Cys Ser Arg Pro
 1                   5                  10                  15
Lys Val Ala Ala Leu Thr Ala Gly Thr Leu Leu Leu Leu Thr Ala Ile
             20                  25                  30
Gly Ala Ala Ser Trp Ala Ile Val Ala Val Leu Leu Arg Ser Asp Gln
         35                  40                  45
Glu Pro Leu Tyr Pro Val Gln Val Ser Ser Ala Asp Ala Arg Leu Met
     50                  55                  60
Val Phe Asp Lys Thr Glu Gly Thr Trp Arg Leu Leu Cys Ser Ser Arg
 65                  70                  75                  80
Ser Asn Ala Arg Val Ala Gly Leu Ser Cys Glu Glu Met Gly Phe Leu
             85                  90                  95
Arg Ala Leu Thr His Ser Glu Leu Asp Val Arg Thr Ala Gly Ala Asn
        100                 105                 110
Gly Thr Ser Gly Phe Phe Cys Val Asp Glu Gly Arg Leu Pro His Thr
    115                 120                 125
Gln Arg Leu Leu Glu Val Ile Ser Val Cys Asp Cys Pro Arg Gly Arg
130                 135                 140
Phe Leu Ala Ala Ile Cys Gln Gly Glu Ile Leu Lys Leu Arg Thr Leu
    145                 150                 155                 160
Ser Phe Arg Pro Leu Gly Arg Pro Arg Pro Leu Lys Pro Arg Met
        165                 170                 175
Gly Pro Cys Thr Phe Arg Pro Pro Arg Ala Gly Pro Ser Leu Gly Ser
    180                 185                 190
Gly Asp Leu Gly Ser Ser Pro Leu Ser Pro Pro Ala Asp Pro Cys
        195                 200                 205
Pro Thr Asp Cys Gly Arg Arg Lys Leu Pro Val Asp Arg Ile Val Gly
    210                 215                 220
Gly Arg Asp Thr Ser Leu Gly Arg Trp Pro Trp Gln Val Ser Leu Arg
225                 230                 235                 240
```

FIG. 8B

Tyr Asp Gly Ala His Leu Cys Gly Gly Ser Leu Leu Ser Gly Asp Trp
                245                 250                 255
Val Leu Thr Ala Ala His Cys Phe Pro Glu Arg Asn Arg Val Leu Ser
        260                 265                 270
Arg Trp Arg Val Phe Ala Gly Ala Val Ala Gln Ala Ser Pro His Gly
    275                 280                 285
Leu Gln Leu Gly Val Gln Ala Val Val Tyr His Gly Tyr Gly Tyr Leu Pro
290                 295                 300
Phe Arg Asp Pro Asn Ser Glu Gln Asn Ser Asn Asp Ile Ala Leu Val
305                 310                 315                 320
His Leu Ser Ser Pro Leu Pro Leu Thr Glu Tyr Ile Gln Pro Val Cys
        325                 330                 335
Leu Pro Ala Ala Gly Gln Ala Leu Val Asp Gly Lys Ile Cys Thr Val
    340                 345                 350
Thr Gly Trp Gly Asn Thr Gln Tyr Tyr Gly Gln Gln Ala Gly Val Leu
355                 360                 365
Gln Glu Ala Arg Val Pro Ile Ile Ser Asn Asp Val Cys Asn Gly Ala
        370                 375                 380
Asp Phe Tyr Gly Asn Gln Ile Lys Pro Lys Met Phe Cys Ala Gly Tyr
385                 390                 395                 400
Pro Glu Gly Gly Ile Asp Ala Cys Gln Gly Asp Ser Gly Gly Pro Phe
        405                 410                 415
Val Cys Glu Asp Ser Ile Ser Arg Thr Pro Arg Trp Arg Leu Cys Gly
    420                 425                 430
Ile Val Ser Trp Gly Thr Gly Cys Ala Leu Ala Gln Lys Pro Gly Val
435                 440                 445
Tyr Thr Lys Val Ser Asp Phe Arg Glu Trp Ile Phe Gln Ala Ile Lys
        450                 455                 460
Thr His Ser Glu Ala Ser Gly Met Val Thr Gln Leu
465                 470                 475

(SEQ ID NO:2)

METHODS AND COMPOSITIONS FOR MODULATING HEPATOCYTE GROWTH FACTOR ACTIVATION

RELATED APPLICATIONS

This application is a non-provisional application filed under 37 CFR 1.53(b)(1), claiming priority under 35 USC 119(e) to provisional application No. 60/591,339 filed Jul. 26, 2004, the contents of which are incorporated herein by reference.

TECHNICAL FIELD

The present invention relates generally to the fields of molecular biology and growth factor regulation. More specifically, the invention concerns modulators of the HGF/c-met signaling pathway, and uses of said modulators.

BACKGROUND

Hepsin (also known as TMRPRSS1) is a cell surface expressed chymotrypsin-like serine protease and a member of the family of type II transmembrane serine proteases (TTSP), which also include matriptase (also known as MT-SP1) and enteropeptidase (1). The human hepsin gene, located on chromosome 19 at q11-13.2 (2), encodes a 417 amino acid polypeptide (3) comprised of a short N-terminal cytoplasmic tail, a transmembrane region and an extracellular domain (Arg45-Leu417) composed of the scavenger receptor cysteine-rich (SRCR) and protease domains. Hepsin zymogen is activated autocatalytically by cleavage at Arg162-Ile163 (4), forming a heterodimeric enzyme with the protease domain disulfide-linked (Cys153-Cys277) to the SRCR domain. In addition to the covalent Cys-Cys bond, the recently determined crystal structure of hepsin revealed that SRCR and protease domains share an extensive interface region, each domain burying about 1200 Å$^2$ (5). Because this interface region is located near membrane-proximal residues of the SRCR domain, the hepsin protease domain and active site may be positioned close to the cell surface (5). This is fundamentally different from other cell surface-assembled serine proteases, such as coagulation factors VIIa (FVIIa)$^1$, IXa and Xa, whose active sites are located far above (60-80 Å) the membrane surface (6-8).

The physiological function of hepsin has been elusive. Except for coagulation factor VII, no macromolecular substrates are known and physiologically relevant inhibitors have not been identified. A role of hepsin in blood coagulation was suggested by Kazama et al. (1995) (9) demonstrating that hepsin-transfected cells can activate coagulation factor VII. However, hepsin-deficient mice were viable and showed no blood coagulation disorders (10,11), casting doubt on the importance of hepsin in normal hemostasis. However, it is possible that hepsin may contribute to fibrin formation in pathologic situations, such as renal cell carcinoma (12), where the primary initiator of blood coagulation, tissue factor, (13,14), is absent. Furthermore, other studies have suggested a functional link between hepsin and cellular growth. Depending on the tumor cell line and experimental conditions used, hepsin has been reported to have growth promoting (15) or growth suppressing activity (16). Additional information regarding hepsin can be found in, inter alia, PCT Pub. No. WO2004/009803; U.S. Pat. Nos. 6,482,630; 6,423,543; 5,981,830; U.S. Pat. Appl. Pub. No. 2004/0009911 A1; U.S. Pat. Appl. Pub. No. 2004/0001801 A1; U.S. Pat Appl. Pub. No. 2003/0223973 A1; U.S. Pat. Appl. Pub. No. 2003/0175736 A1; U.S. Pat. Appl. Pub. No. 2003/0013097 A1 (also WO02/059373); U.S. Pat. Appl. Pub. No. 2003/0049645 (also WO02/064839); and U.S. Pat. Appl. Pub. No. 2004/0132156.

Recent gene expression experiments identified hepsin as one of the most highly upregulated genes in prostate cancer (17-22). In-situ staining showed hepsin expression on epithelial cells of the prostate secretory glands (19). The expression of hepsin correlated with the neoplastic transformation (19), being highest in tumors of patients with advanced disease and lowest in benign hyperplasia (18,22). In contrast, one study found that low expression of hepsin protein correlated with high Gleason scores and large tumors (20). It is not clear whether this apparent contradiction is related to the methods used, i.e. immunohistochemistry (20) vs. RNA quantification (18,22). Furthermore, hepsin is also strongly upregulated in ovarian cancer (23) and in renal cell carcinoma, where it is mainly associated with the epithelial cell type (12).

At the epithelial cell surface, hepsin is ideally situated to interact with components of the extracellular matrix and other membrane associated proteins. Chymotrypsin-like serine proteases, including the TTSP matriptase (synonym MT-SP1) (24,25) which is structurally related to hepsin, are known to activate fibrinolytic enzymes, matrix metalloproteases and latent forms of growth factors, such as hepatocyte growth factor (HGF). HGF promotes cell proliferation, migration, angiogenesis, survival and morphogenesis by activating the receptor tyrosine kinase Met (reviewed in (26,27)). In addition to its importance in normal physiology, the HGF/Met pathway has been implicated in invasive tumor growth and tumor metastasis (26). HGF has high similarity to the serine protease plasminogen and is composed of a α-chain containing an N-domain and four Kringle domains and a β-chain with homology to chymotrypsin-like proteases. It is secreted into the extracellular matrix as an inactive single chain precursor (pro-HGF) and requires activation cleavage at Arg494-Val495 to form the biologically competent, disulfide-linked α/β heterodimer (28-31). This step is mediated by pro-HGF converting serine proteases, such as hepatocyte growth factor activator (HGFA) (32), matriptase (33,34), urokinase-type plasminogen activator (u-PA) (35), factor XIIa (36), factor XIa and plasma kallikrein (34). HGFA and matriptase are inhibited by cell surface-expressed Kunitz-type inhibitors, such as the two hepatocyte growth factor activator inhibitor splice variants HAI-1 (37,38) and HAI-1B (34) and by HAI-2 (39). HAI-2 (also known as placental bikunin) (40) also potently inhibits factor XIa and plasma kallikrein (41), whereas HAI-1B has little or no inhibitory activity (34). Therefore, the biological availability of the pro-HGF pool in the extracellular matrix is regulated by the activities of pro-HGF convertases and their inhibitors.

The expression profile of hepsin in cancer tissues as described above, coupled with its potential role in acting as a regulator of other growth factors the dysregulation of which might underlie carcinogenesis suggests that modulation of hepsin's interaction with its substrate could prove to be an efficacious therapeutic approach. In this regard, there is a clear need to identify hepsin's physiological substrate and/or its physiological modulator(s). The invention fulfills this need and provides other benefits.

All references cited herein, including patent applications and publications, are incorporated by reference in their entirety.

DISCLOSURE OF THE INVENTION

As described herein, a physiological substrate for hepsin, a cell-surface protein highly overexpressed in multiple cancers, is hepatocyte growth factor, which itself is known to play an important role in many aspects of cancer development. Hepsin is shown herein to cleave pro-HGF with an activity comparable to the potent physiological pro-HGF convertase, HGFA (hepatocyte growth factor activator). The two-chain (activated) HGF generated by hepsin exhibits normal biological activities, including induction of Met tyrosine phosphorylation, stimulation of cell proliferation, and stimulation of cell migration. In addition, two Kunitz domain inhibitors, HAI-1B and HAI-2, are identified herein as physiological regulators of hepsin enzymatic activity. The invention provides methods and compositions based at least in part on these findings, which are described in greater detail below. It is shown that hepsin and its interaction with HGF and/or its physiological inhibitors can be a unique and advantageous target for greater fine-tuning in designing prophylatic and/or therapeutic approaches against pathological conditions associated with abnormal or unwanted signaling of the HGF/Met (also referred to as "c-met") pathway. Thus, the invention provides methods, compositions, kits and articles of manufacture for identifying and for using substances that are capable of modulating the HGF/c-met pathway through modulation of physiological interacting molecules involved in the regulation of HGF activation.

Accordingly, in one aspect, the invention provides a method of screening for (or identifying) a candidate inhibitor (i.e., antagonist) substance that inhibits hepsin activation of HGF, said method comprising: (a) contacting a candidate substance with a first sample comprising hepsin and a pro-HGF substrate, and (b) comparing amount of pro-HGF substrate activation in the sample with amount of pro-HGF substrate activation in a reference sample comprising similar amounts of hepsin and pro-HGF substrate as the first sample but that has not been contacted with said candidate substance, whereby a decrease in amount of pro-HGF substrate activation in the first sample compared to the reference sample indicates that the candidate substance is capable of inhibiting hepsin activation of single chain HGF (pro-HGF). In one embodiment, hepsin in a sample is in an effective amount for activating said pro-HGF. A pro-HGF substrate suitable for use in these methods can be in a number of forms, so long as it mimics the characteristic of the hepsin cleavage site on pro-HGF. Examples of pro-HGF substrate include, but are not limited to, full length single chain HGF comprising a wild type form of the R494-V495 peptide linkage, and any fragment of HGF that comprises this peptide linkage. Such fragment can be any length, for example at least (about) 5, 7, 10, 15, 20, 25 amino acids in length, or between (about) 4 and 25, 5 and 20, 7 and 15 amino acids in length. Generally and preferably, a pro-HGF substrate comprises a R494-V495 peptide bond capable of being cleaved by wild type hepsin. In one embodiment, the pro-HGF substrate comprises a cleavage site of human HGF that fits the consensus cleavage site of proteases (i.e., basic residue at position $P_1$ and two hydrophobic amino acid residues in positions $P_1'$ and $P_2'$-$P_1$ R494, $P_1'$ V495, $P_2'$ V496).

In another aspect, the invention provides a method of screening for a substance that blocks pro-HGF activation by hepsin, said method comprising screening for a substance that binds (preferably, but not necessarily, specifically) hepsin or pro-HGF and blocks specific interaction (e.g., binding) between hepsin and pro-HGF. In some embodiments, the substance competes with hepsin for binding to HGF. In some embodiments, the substance competes with pro-HGF for binding to hepsin. In one embodiment, the substance comprises, consists or consists essentially of an amino acid sequence having at least about 60%, 70%, 80%, 90%, 95%, 99% sequence similarity or identity with respect to pro-HGF (e.g., human), e.g., a fragment of human HGF comprising amino acid residues 494(Arg) peptide linked to 495(Val). In some embodiments wherein the substance comprises, consists or consists essentially of such an amino acid sequence, the fragment is mutated or devoid of at least a portion of HGF beta chain, such that said fragment has reduced c-met activating activity compared to wild type HGF.

As would be evident to one skilled in the art, screening assays consistent with those described above can also comprise a first step of screening based on a hepsin-HGF complex formation readout to obtain a first set of candidate modulatory substance, followed by a second step of screening based on ability of the first set of candidate modulatory substance to modulate activation of HGF and/or conversion of HGF into a form that is capable of activating the HGF/c-met pathway. Suitable readouts can be any that would be evident to one skilled in the art, based on a knowledge of enzyme-substrate complex formation and/or biological activities associated with the HGF/c-met signaling pathway. Enzyme-substrate complex formation can be measured using, for example, routine biochemical assays (e.g., gel electrophoresis, chromatography, NMR, etc.). HGF/c-met biological activities include but are not limited to C-met phosphorylation, phosphorylation of cellular molecules that are substrates of C-met kinase, cellular growth (proliferation, survival, etc.), angiogenesis, cell migration, cell morphogenesis, etc.

In one aspect, the invention provides HGF/c-met antagonists that disrupt the HGF/c-met signaling pathway. For example, the invention provides a molecule that inhibits hepsin cleavage of pro-HGF (e.g., cleavage at the R494-V495 position). The molecule can exert its inhibitory function in any number of ways, including but not limited to binding to either hepsin or pro-HGF such that hepsin cleavage of pro-HGF is inhibited, binding to hepsin-pro-HGF complex such that cleavage of pro-HGF is inhibited, and/or binding to pro-HGF or hepsin (singly or in complex) such that effects of HGF cleavage by hepsin is inhibited (e.g., inhibition of release of HGF subsequent to cleavage by hepsin). In one embodiment, an antagonist molecule of the invention does not inhibit HGF binding to c-met. For example, in one embodiment, an antagonist molecule of the invention is not an antibody or fragment thereof having similar inhibitory and/or binding ability as the antibody produced by hybridoma cell line deposited under American Type Culture Collection Accession Number ATCC HB-11894 (hybridoma 1A3.3.13) or HB-11895 (hybridoma 5D5.11.6). In one embodiment, an antagonist molecule of the invention inhibits biological activities associated with HGF/c-met activation.

In one aspect, an antagonist of the invention is derived from the discovery described herein that hepatocyte growth factor activator inhibitors (HAI-1, HAI-1B, HAI-2) are potent inhibitors of hepsin activation of pro-HGF. In one embodiment, the invention provides an antagonist of pro-HGF activation by hepsin, said antagonist comprising at least a portion (including all) of human HAI-1, HAI-1B or HAI-2. In one embodiment, said portion comprises a Kunitz domain (KD) sequence capable of inhibiting pro-HGF activation by hepsin. In one embodiment, said Kunitz domain sequence is Kunitz domain 1 (KD1) of HAI-1 or HAI-1B. In one embodiment, an antagonist of the invention comprises a variant KD1 sequence having at least about 70%, 75%, 80%, 85%, 90%, 95%, 97%, 98%, 99% sequence identity with wild type KD1 of human HAI-1, wherein said variant sequence has at least comparable ability as wild type KD1 in inhibiting hepsin cleavage of human pro-HGF. In one embodiment, an antagonist of the invention comprises a variant KD1 sequence having between about 70% and 99%, about 75% and 98%, about 80% and 97%, 85% and 95% sequence identity with wild type KD1 of human HAI-1, wherein said sequence has at least comparable ability as wild type KD1 in inhibiting hepsin cleavage of human pro-HGF. In one embodiment, said Kunitz domain sequence is one or both of the Kunitz domains of HAI-2. In one embodiment, an antagonist of the invention comprises a variant HAI-2 Kunitz domain sequence having at least about 70%, 75%, 80%, 85%, 90%, 95%, 97%, 98%, 99% sequence identity with the corresponding Kunitz domain(s) of wild type human HAI-2, wherein said variant sequence has at least comparable ability as wild type HAI-2 in inhibiting hepsin cleavage of human pro-HGF. In one embodiment, an antagonist of the invention comprises a variant HAI-2 Kunitz domain sequence having between about 70% and 99%, about 75% and 98%, about 80% and 97%, 85% and 95% sequence identity with the corresponding Kunitz domain(s) of wild type human HAI-2, wherein said sequence has at least comparable ability as wild type HAI-2 in inhibiting hepsin cleavage of human pro-HGF.

In some embodiments, an antagonist of the invention is or comprises a small molecule, peptide, antibody, antibody fragment, aptamer, or a combination thereof. Antagonists as described herein can be routinely obtained using techniques known in the art (including those described in greater detail below) based on the discovery of the interaction of hepsin, hepatocyte growth factor activator inhibitors and pro-HGF as described herein. For example, in some embodiments, an antagonist of the invention competes with hepsin for binding to HGF, but does not have ability to cleave pro-HGF at the hepsin cleavage site. In some embodiments, an antagonist of the invention competes with pro-HGF for binding to hepsin. For example, in one embodiment, said antagonist comprises, consists or consists essentially of an amino acid sequence having at least about 60%, 70%, 80%, 90%, 95%, 98%, 99% sequence similarity or identity with respect to pro-HGF (e.g., human) and is capable of substantially binding hepsin, but lacks a hepsin cleavage site (e.g., a $P_1$ site comprising the wild type human HGF R494-V495 peptide link) and/or lacks ability to activate c-met (e.g., wherein the HGF β chain is mutated, is devoid of HGF β chain or portion thereof, etc.). In one embodiment, an antagonist of the invention comprises, consists or consists essentially of an HGF fragment capable of binding hepsin, wherein said fragment is devoid of at least a portion of HGF β chain such that said fragment has reduced c-met activating activity compared to wild type HGF.

Thus, the invention provides an HGF mutant capable of substantially binding hepsin but has decreased HGF/c-met modulatory activity compared to wild type HGF, e.g. an antagonist of HGF/c-met activity or an HGF variant exhibiting a reduction, but not an absence, of HGF biological activity (e.g., cell growth stimulatory activity). In one embodiment, an antagonist of the invention is capable of inhibiting the biological activity of wild type (in vivo) HGF (such biological activity includes but is not limited to stimulation of cell proliferation, enhancement of cell survival, promotion of angiogenesis, induction/promotion of cell migration). In one embodiment, an antagonist of the invention provides reduced cell growth (including but not limited to cell proliferation, cell survival, angiogenic, cell migration) promoting activity.

In some embodiments, an antagonist of the invention is obtained by a screening or identification method of the invention as described herein.

In one aspect, an antagonist molecule of the invention is linked to a toxin such as a cytotoxic agent. These molecules/substances can be formulated or administered in combination with an additive/enhancing agent, such as a radiation and/or chemotherapeutic agent.

In one aspect, the invention provides a molecule capable of enhancing pro-HGF cleavage by hepsin, wherein said molecule is capable of interfering with HAI-1, HAI-1B and/or HAI-2 interaction with hepsin. In some embodiments, an enhancer molecule of the invention is or comprises a small molecule, peptide, antibody, antibody fragment, aptamer, or a combination thereof. For example, an enhancer molecule of the invention may comprise, consist, or consist essentially of a fragment, or variant thereof, of HAI-1, HAI-1B and/or HAI-2, wherein said fragment is capable of binding to hepsin but does not substantially inhibit hepsin cleavage of pro-HGF. In one embodiment, said molecule is capable of competitively inhibiting binding of wild type HAI-1, HAI-1B and/or HAI-2 to hepsin. In one embodiment, an enhancer molecule of the invention is an antibody that interferes with formation of a complex comprising hepsin and HAI-1, HAI-1B and/or HAI-2. In one embodiment, an enhancer molecule of the invention is hepsin or variant thereof (including any of those defined below), wherein the hepsin or variant thereof is capable of effecting pro-HGF cleavage at the R494-V495 site.

The invention also provides methods and compositions useful for modulating disease states associated with dysregulation of the HGF/c-met signaling axis. Thus, in one aspect, the invention provides a method of modulating c-met activation in a subject, said method comprising administering to the subject an HGF/c-met modulator molecule of the invention (e.g., an antagonist molecule, as described herein, that inhibits hepsin cleavage of pro-HGF), whereby c-met activation is modulated. In one embodiment, said molecule is an HGF/c-met antagonist that inhibits HGF/c-met activity. In one embodiment, said molecule is an enhancer molecule that increases HGF/c-met activity. In one aspect, the invention provides a method of treating a pathological condition associated with activation of c-met in a subject, said method comprising administering to the subject a c-met antagonist of the invention (e.g., any of the antagonists of pro-HGF cleavage by hepsin as described herein), whereby c-met activation is inhibited.

The HGF/c-met signaling pathway is involved in multiple biological and physiological functions, including, e.g., cell growth stimulation (e.g. cell proliferation, cell survival, cell migration, cell morphogenesis) and angiogenesis. Thus, in another aspect, the invention provides a method of inhibiting c-met activated cell growth (e.g. proliferation and/or survival), said method comprising contacting a cell or tissue with an antagonist of the invention, whereby cell proliferation associated with c-met activation is inhibited. In yet another aspect, the invention provides a method of inhibiting angiogenesis, said method comprising administering to a cell, tissue, and/or subject with a condition associated with abnormal angiogenesis an antagonist of the invention, whereby angiogenesis is inhibited. In yet another aspect, the invention provides a method of enhancing angiogenesis, said method comprising administering to a cell, tissue, and/or subject with a condition that would benefit from increased angiogenesis and/or is associated with sub-optimal amount of angiogenesis an enhancer molecule of the invention, whereby angiogenesis is enhanced.

In one aspect, the invention provides use of an antagonist of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder. The antagonist can be of any form described herein, including antibody, antibody fragment, small molecule (e.g., an organic molecule), polypeptide (e.g., an oligopeptide), nucleic acid (e.g., an oligonucleotide, such as an antisense oligonucleotide or interefering RNA), an aptamer, or combination thereof.

In one aspect, the invention provides use of an enhancer molecule of the invention in the preparation of a medicament for the therapeutic and/or prophylactic treatment of a disease, such as wound healing (e.g., wounds associated with diabetes, trauma, etc.). The enhancer molecule can be of any form described herein, including antibody, antibody fragment, small molecule (e.g., an organic molecule), polypeptide (e.g., an oligopeptide), nucleic acid (e.g., an oligonucleotide, such as an antisense oligonucleotide or interfering RNA), an aptamer, or combination thereof.

In one aspect, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder (e.g., wound healing).

In one aspect, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder (e.g., wound healing).

In one aspect, the invention provides use of a host cell of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder (e.g., wound healing).

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder (wound healing).

In one aspect, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder (wound healing).

In one aspect, the invention provides a method of inhibiting c-met activated cell proliferation, said method comprising contacting a cell or tissue with an effective amount of an antagonist of the invention, whereby cell proliferation associated with c-met activation is inhibited.

In one aspect, the invention provides a method of treating a pathological condition associated with dysregulation of c-met activation in a subject, said method comprising administering to the subject an effective amount of an antagonist of the invention, whereby said condition is treated.

In one aspect, the invention provides a method of inhibiting the growth of a cell that expresses c-met or hepatocyte growth factor, or both, said method comprising contacting said cell with an antagonist of the invention thereby causing an inhibition of growth of said cell. In one embodiment, the cell is contacted by HGF expressed by a different cell (for e.g., through a paracrine effect).

In one aspect, the invention provides a method of therapeutically treating a mammal having a cancerous tumor comprising a cell that expresses c-met or hepatocyte growth factor, or both, said method comprising administering to said mammal an effective amount of an antagonist of the invention, thereby effectively treating said mammal. In one embodiment, the cell is contacted by HGF expressed by a different cell (e.g., through a paracrine effect).

In one aspect, the invention provides a method for treating or preventing a cell proliferative disorder associated with increased expression or activity of hepsin, c-met and/or hepatocyte growth factor, said method comprising administering to a subject in need of such treatment an effective amount of an antagonist of the invention, thereby effectively treating or preventing said cell proliferative disorder. In one embodiment, said proliferative disorder is cancer.

In one aspect, the invention provides a method for inhibiting the growth of a cell, wherein growth of said cell is at least in part dependent upon a growth potentiating effect of hepsin, c-met and/or hepatocyte growth factor, said method comprising contacting said cell with an effective amount of an antagonist of the invention, thereby inhibiting the growth of said cell. In one embodiment, the cell is contacted by HGF expressed by a different cell (e.g., through a paracrine effect).

In one aspect, the invention provides a method of therapeutically treating a tumor in a mammal, wherein the growth of said tumor is at least in part dependent upon a growth potentiating effect of hepsin, c-met and/or hepatocyte growth factor, said method comprising contacting said cell with an effective amount of an antagonist of the invention, thereby effectively treating said tumor. In one embodiment, the cell is contacted by HGF expressed by a different cell (e.g., through a paracrine effect).

Methods of the invention can be used to affect any suitable pathological state, for example, cells and/or tissues associated with dysregulation of the hepsin and/or HGF/c-met signaling pathway. In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell (e.g., of the thyroid gland), a colon cancer cell, a pancreatic cancer cell, an ovarian cancer cell, a cervical cancer cell, a central nervous system cancer cell, a prostate cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell and a leukemia cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

As described herein, c-met activation is an important biological process the dysregulation of which leads to numerous pathological conditions. Accordingly, in one embodiment of methods of the invention, a cell that is targeted (e.g., a cancer cell) is one in which activation of c-met is enhanced as compared to a normal cell of the same tissue origin. In one embodiment, a method of the invention causes the death of a targeted cell. For example, contact with an antagonist of the invention may result in a cell's inability to signal through the c-met pathway, which results in cell death.

Dysregulation of c-met activation (and thus signaling) can result from a number of cellular changes, including, for example, overexpression of HGF (c-met's cognate ligand) and/or c-met itself. Accordingly, in some embodiments, a method of the invention comprises targeting a cell wherein c-met or hepatoctye growth factor, or both, is more abundantly expressed by said cell (e.g., a cancer cell) as compared to a normal cell of the same tissue origin. A c-met-expressing cell can be regulated by HGF from a variety of sources, i.e. in an autocrine or paracrine manner. For example, in one embodiment of methods of the invention, a targeted cell is contacted/bound by hepatocyte growth factor expressed in a different cell (e.g., via a paracrine effect). Said different cell can be of the same or of a different tissue origin. In one embodiment, a targeted cell is contacted/bound by HGF expressed by the targeted cell itself (e.g., via an autocrine effect/loop).

In one aspect, the invention provides a method comprising administering to a subject an enhancer molecule of the invention. Suitable conditions to be treated by this method include any pathological conditions that are associated with an abnormally/undesirably low physiological level of angiogenesis associated with HGF/c-met activity in a subject. Examples of such conditions include but are not limited to wound healing, cardiac hypertrophy, cardiac infarction, limb ischemia, peripheral arterial disease, etc.

In one aspect, the invention provides compositions comprising one or more antagonists or enhancers of the invention and a carrier. In one embodiment, the carrier is pharmaceutically acceptable.

In one aspect, the invention provides nucleic acids encoding an antagonist or enhancer molecule of the invention. In one embodiment, a nucleic acid of the invention encodes an antagonist or enhancer molecule which is or comprises a polypeptide (e.g., an oligopeptide). In one embodiment, a nucleic acid of the invention encodes an antagonist or enhancer molecule which is or comprises an antibody or fragment thereof.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antagonist or enhancer molecule of the invention. For example, the invention provides a method of making an antagonist which is or comprises an antibody (or fragment thereof), said method comprising expressing in a suitable host cell a recombinant vector of the invention encoding said antibody (or fragment thereof), and recovering said antibody. In another example, the invention provides a method of making an antagonist or enhancer molecule which is or comprises a polypeptide (such as an oligopeptide), said method comprising expressing in a suitable host cell a recombinant vector of the invention encoding said polypeptide (such as an oligopeptide), and recovering said polypeptide (such as an oligopeptide).

In one aspect, the invention provides an article of manufacture comprising a container; and a composition contained within the container, wherein the composition comprises one or more antagonists or enhancer molecules of the invention. In one embodiment, the composition comprises a nucleic acid of the invention. In one embodiment, a composition comprising an antagonist or enhancer molecule further comprises a carrier, which in some embodiments is pharmaceutically acceptable. In one embodiment, an article of manufacture of the invention further comprises instructions for administering the composition (e.g., the antagonist or enhancer molecule) to a subject.

In one aspect, the invention provides a kit comprising a first container comprising a composition comprising one or more antagonists or enhancer molecules of the invention; and a second container comprising a buffer. In one embodiment, the buffer is pharmaceutically acceptable. In one embodiment, a composition comprising an antagonist or enhancer molecule further comprises a carrier, which in some embodiments is pharmaceutically acceptable. In one embodiment, a kit further comprises instructions for administering the composition (e.g., the antagonist or enhancer molecule) to a subject.

BRIEF DESCRIPTION OF THE DRAWINGS

FIG. 1 Hepsin purity and activity towards factor VII. (A) The CHO cell-expressed soluble hepsin comprised the entire extracellular domain (Arg45-Leu417) and a C-terminal $His_8$ tag. Stained gels (reducing conditions) of purified hepsin shows that hepsin had spontaneously converted into its two-chain form by cleavage at Arg163-Ile163 (verified by N-terminal sequencing). (B) Activation of factor VII zymogen by hepsin (40 nM) in the presence of PCPS vesicles and $CaCl_2$ at 37° C. during a 2 h period. The positions of FVII zymogen as well as the light chain (l.c.) and protease domain (h.c.) of FVIIa are indicated. Molecular weight markers are shown as $M_r \times 10^{-3}$.

FIG. 2 Specific activation of pro-HGF by hepsin. $^{125}$I-labelled pro-HGF (0.05 mg/ml) was incubated in 20 mM Hepes, pH 7.5, 150 mM NaCl (Hepes buffer) with decreasing concentrations of hepsin and HGFA: 3-fold dilution steps of enzymes, from 40 nM in lane 2 down to 0.16 nM in lane 7. (A) Hepsin and (B) HGFA. After 4 h at 37° C. the samples were analyzed by SDS-PAGE under reducing conditions followed by exposure to x-ray films. The positions of pro-HGF, HGF α-chain and HGF β-chain (doublet) are indicated. Lane 1 is an aliquot immediately taken at the beginning of the reaction. (C) Activation of plasminogen by t-PA and hepsin. Plasminogen (0.12 mg/ml) was incubated with t-PA (40 nM), hepsin (40 nM) or buffer (control) in Hepes buffer. Aliquots taken at different time points were analyzed by SDS-PAGE (reducing conditions) followed by staining with Simply Blue Safe Stain. Lane 1, buffer at 0.5 h; lane 2, t-PA at 0.5 h; lane 3, hepsin at 0.5 h; lane 4, buffer at 5 h; lane 5, t-PA at 5 h; lane 6, hepsin at 5 h. The positions of plasminogen (Plg) and the plasmin heavy chain (h.c) are indicated.

FIG. 3 Phosphorylation of Met by pro-HGF activated by hepsin and HGFA. (A) Unlabelled pro-HGF (0.3 mg/ml) was cleaved with 40 nM hepsin or 40 nM HGFA yielding >95% conversion. HGF produced by hepsin cleavage ($HGF_{hepsin}$) and by HGFA cleavage ($HGF_{HGFA}$) were analyzed by SDS-PAGE (reducing conditions) and stained with Simply Blue Safe Stain. (B) Phosphorylation of Met receptor was measured in a KIRA assay by exposing A549 cells to increasing concentrations of $HGF_{hepsin}$ (circles), $HGF_{HGFA}$ (squares), or to scHGF (diamonds), an uncleavable single-chain form of HGF. The activities were expressed as percent of the maximal signal obtained with an HGF control preparation. Values are the average ±SD of three experiments.

FIG. 4 Cell proliferation and migration with pro-HGF activated by hepsin ($HGF_{hepsin}$) and HGFA ($HGF_{HGFA}$). (A) Cell proliferation of BxPC3 cells in the presence of increasing concentrations of $HGF_{hepsin}$ (filled bars) and $HGF_{HGFA}$ (open bars). Values are the average of two experiments. (B) Quantification of cell migration stimulated by increasing concentrations of $HGF_{hepsin}$ (filled bars) and $HGF_{HGFA}$ (open bars) added to the lower chamber of a transwell cell migration system. Values are the average ±SD of three experiments. Activities in proliferation and migration assays were expressed as percent of control cells exposed to 100 ng/ml of a control HGF preparation, which was included in each experiment.

FIG. 5 Inhibition of hepsin enzymatic activity in an amidolytic assay. Hepsin (0.4 nM) was incubated with inhibitors for 30 min at room temperature and enzymatic activity towards S2366 (0.2 mM~$K_m$) was determined on a kinetic microplate reader. (■), sHAI-1B, (▼), sHAI-1B (R260A), (●), sHAI-1B(K401A), (●), sHAI-2.

FIG. 6 Inhibition of pro-HGF activation by mutant forms of sHAI-1B and by sHAI-2. $^{125}$I-labelled pro-HGF (0.05 mg/ml) was incubated with hepsin (15 nM) and inhibitors for 4 h at 37° C. Reaction aliquots were analyzed as described in FIG. 1. Hepsin at 15 nM was present in each sample. Inhibitors were at 1 µM. Lane 1, aliquot at t=0; 2, no inhibitor; 3, sHAI-1B; 4, sHAI-1B(R260A); 5, sHAI-1B(K401A); 6, sHAI-2. The positions of pro-HGF, HGF α-chain and HGF β-chain (doublet) are indicated.

FIG. 7 One embodiment of an amino acid sequence of native human hepsin.

FIG. 8 Another embodiment of an amino acid sequence of native human hepsin.

MODES FOR CARRYING OUT THE INVENTION

The invention provides methods, compositions, kits and articles of manufacture comprising modulators of the HGF/c-met signaling pathway, including methods of using such modulators.

Details of these methods, compositions, kits and articles of manufacture are provided herein.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

Definitions

The term "hepsin" as used herein encompasses native sequence polypeptides, polypeptide variants and fragments of a native sequence polypeptide and polypeptide variants (which are further defined herein) that is capable of pro-HGF cleavage in a manner similar to wild type hepsin. The hepsin polypeptide described herein may be that which is isolated from a variety of sources, such as from human tissue types or from another source, or prepared by recombinant or synthetic methods. The terms "hepsin", "hepsin polypeptide", "hepsin enzyme", and "hepsin protein" also include variants of a hepsin polypeptide as disclosed herein.

A "native sequence hepsin polypeptide" comprises a polypeptide having the same amino acid sequence as the corresponding hepsin polypeptide derived from nature. In one embodiment, a native sequence hepsin polypeptide comprises the amino acid sequence of SEQ ID NO:1 (see FIG. 7). In one embodiment, a native sequence hepsin polypeptide comprises the amino acid sequence of SEQ ID NO:2 (see FIG. 8). Such native sequence hepsin polypeptide can be isolated from nature or can be produced by recombinant or synthetic means. The term "native sequence hepsin polypeptide" specifically encompasses naturally-occurring truncated or secreted forms of the specific hepsin polypeptide (e.g., an extracellular domain sequence), naturally-occurring variant forms (e.g., alternatively spliced forms) and naturally-occurring allelic variants of the polypeptide.

"Hepsin polypeptide variant", or variations thereof, means a hepsin polypeptide, generally an active hepsin polypeptide, as defined herein having at least about 80% amino acid sequence identity with any of the native sequence hepsin polypeptide sequences as disclosed herein. Such hepsin polypeptide variants include, for instance, hepsin polypeptides wherein one or more amino acid residues are added, or deleted, at the N- or C-terminus of a native amino acid sequence. Ordinarily, a hepsin polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence hepsin polypeptide sequence as disclosed herein. Ordinarily, hepsin variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, hepsin variant polypeptides will have no more than one conservative amino acid substitution as compared to a native hepsin polypeptide sequence, alternatively no more than 2, 3, 4, 5, 6, 7, 8, 9, or 10 conservative amino acid substitution as compared to the native hepsin polypeptide sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, as described in U.S. Pat. No. 6,828,146.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR.sub.2 ("amidate"), P(O)R, P(O)OR', CO or CH.sub.2 ("formacetal"), in which each R or R' is independently H or substituted or unsubstituted alkyl (1-20 C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "hepatocyte growth factor" or "HGF", as used herein, refers, unless specifically or contextually indicated otherwise, to any native or variant (whether naturally occurring or synthetic) HGF polypeptide that is capable of activating the HGF/c-met signaling pathway under conditions that permit such process to occur. The term "wild type HGF" generally refers to a polypeptide comprising the amino acid sequence of a naturally occurring HGF protein. Thet term "wild type HGF sequence" generally refers to an amino acid sequence found in a naturally occurring HGF.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-inmidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELE-BREX®; 4-(5-(4-methylphenyl)-3-(trifluoromethyl)-1H-pyrazol-1-yl) benzenesulfonamide; and pharmaceutically acceptable salts, acids or derivatives of any of the above.

A "growth inhibitory agent" when used herein refers to a compound or composition which inhibits growth of a cell whose growth is dependent upon HGF/c-met activation either in vitro or in vivo. Thus, the growth inhibitory agent may be one which significantly reduces the percentage of HGF/c-met-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

COMPOSITIONS AND METHODS OF THE INVENTION

A. Antibodies

In one embodiment, the present invention provides antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ¹⁄₁₀ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.*, 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp.59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl Acad. Sci. USA*, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. Coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of hepsin, HGF and/or hepsin:HGF complex as described herein. Other such antibodies may combine a binding site on these entities with a binding site for another polypeptide. Alternatively, an antibody arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the hepsin and/or HGF-expressing and/or binding cell. Bispecific antibodies may also be used to localize cytotoxic agents to cells which express and/or bind hepsin, HGF and/or hepsin:HGF complex. These antibodies possess a polypeptide binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HWV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv(sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH—CH1-flexible linker-VH—CH1-Fc region chain; or VH—CH1-VH—CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19): 1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG 1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):433642; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozoganucin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl -4-(N-maleimidomethyl) cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another imrnunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium -90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal,CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl -4-(N-maleimidomethyl) cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antbody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_p \qquad \text{I}$$

Nucleophilic groups on antibodies include, but are not limited to (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic subsituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, *Bioconjugate Techniques*). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide interchange reaction. A chemotherapeutic agent is optionally contained within the liposome. See Gabizon et al., *J. National Cancer Inst.* 81(19): 1484 (1989).

B. Binding Oligopeptides

Binding oligopeptides of the invention are oligopeptides that bind, preferably specifically, to hepsin, HGF and/or hepsin: HGF complex as described herein. Binding oligopeptides may be chemically synthesized using known oligopeptide synthesis methodology or may be prepared and purified using recombinant technology. Binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a polypeptide as described herein. Binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223, 409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) *Science*, 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) *Proc. Natl. Acad. Sci. USA*, 87:6378) or protein (Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A.S. et al. (1991) *Proc. Natl. Acad. Sci. USA*, 88:8363) libraries on phage have been used for screening millions of polypeptides or oligopeptides for ones with specific binding properties (Smith, G. P. (1991) *Current Opin. Biotechnol.*, 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., *Gene*, 215: 439 (1998); Zhu et al., *Cancer Research*, 58(15): 3209-3214 (1998); Jiang et al., *Infection & Immunity*, 65(11): 4770-4777 (1997); Ren et al., Gene, 195(2):303-311 (1997); Ren, *Protein Sci.*, 5: 1833 (1996); Efimov et al., *Virus Genes*, 10: 173 (1995)) and T7 phage display systems (Smith and Scott, *Methods in Enzymology*, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Binding Small Molecules

Binding small molecules are preferably organic molecules other than oligopeptides or antibodies as defined herein that bind, preferably specifically, to hepsin, HGF and/or hepsin: HGF complex as described herein. Binding organic small molecules may be identified and chemically synthesized using known methodology (see, e.g., PCT Publication Nos. WO00/00823 and WO00/39585). Binding organic small molecules are usually less than about 2000 daltons in size, alternatively less than about 1500, 750, 500, 250 or 200 daltons in size, wherein such organic small molecules that are capable of binding, preferably specifically, to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Publication Nos. WO00/00823 and WO00/39585). Binding organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Antibodies, Binding Oligopeptides and Binding Small Molecules with the Desired Properties Techniques for generating antibodies, oligopeptides and small molecules of the invention have been described above. One may further select antibodies, oligopeptides or other small molecules with certain biological characteristics, as desired.

The growth inhibitory effects of an antibody, oligopeptide or other small molecule of the invention may be assessed by methods known in the art, e.g., using cells which express hepsin and/or pro-HGF either endogenously or following transfection with the respective gene(s). For example, appropriate tumor cell lines, and hepsin and/or HGF polypeptide-transfected cells may be treated with a monoclonal antibody, oligopeptide or other small molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an antibody, binding oligopeptide or binding small molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. The tumor cell may be one that overexpresses a hepsin and/or pro-HGF polypeptide. The antibody, binding oligopeptide or binding organic small molecule will inhibit cell proliferation of a hepsin and/or HGF-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the antibody at about 1 μg/kg to about 100 mg/kg body weight results in reduction in tumor size or reduction of tumor cell proliferation within about 5 days to 3 months from the first administration of the antibody, preferably within about 5 to 30 days.

To select for an antibody, binding oligopeptide or binding organic small molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. Hepsin and/or pro-HGF polypeptide-expressing tumor cells are incubated with medium alone or medium containing the appropriate antibody (e.g, at about 10 μg/ml), binding oligopeptide or binding organic small molecule. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those antibodies, binding oligopeptides or binding organic small molecules that induce statistically significant levels of cell death as determined by PI uptake may be selected as cell death-inducing antibodies, binding oligopeptides or binding organic small molecules.

To screen for antibodies, oligopeptides or other organic small molecules which bind to an epitope on a polypeptide bound by an antibody of interest, a routine cross-blocking assay such as that described in *Antibodies. A Laboratory Manual,* Cold Spring Harbor Laboratory, Ed Harlow and David Lane (1988), can be performed. This assay can be used to determine if a test antibody, oligopeptide or other organic small molecule binds the same site or epitope as a known antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984).

F. Antibody Variants

In addition to the antibodies described herein, it is contemplated that antibody variants can be prepared. Antibody variants can be prepared by introducing appropriate nucleotide changes into the encoding DNA, and/or by synthesis of the desired antibody. Those skilled in the art will appreciate that amino acid changes may alter post-translational processes of the antibody, such as changing the number or position of glycosylation sites or altering the membrane anchoring characteristics.

Variations in the antibodies described herein can be made, for example, using any of the techniques and guidelines for conservative and non-conservative mutations set forth, for instance, in U.S. Pat. No. 5,364,934. Variations may be a substitution, deletion or insertion of one or more codons encoding the antibody that results in a change in the amino acid sequence as compared with the native sequence antibody or polypeptide. Optionally the variation is by substitution of at least one amino acid with any other amino acid in one or more of the domains of the antibody. Guidance in determining which amino acid residue may be inserted, substituted or deleted without adversely affecting the desired activity may be found by comparing the sequence of the antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the parent sequence.

Antibody and polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the antibody or polypeptide.

Antibody and polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, antibody and polypeptide fragments share at least one biological and/or immunological activity with the native antibody or polypeptide disclosed herein.

In particular embodiments, conservative substitutions of interest are shown in the table below under the heading of preferred substitutions. If such substitutions result in a change in biological activity, then more substantial changes, denominated exemplary substitutions in this table, or as further described below in reference to amino acid classes, are introduced and the products screened.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the antibody or polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the antibody or polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.* 150:1 (1976)]. If alanine substitution does not yield adequate amounts of variant, an isoteric amino acid can be used.

Any cysteine residue not involved in maintaining the proper conformation of the antibody or polypeptide also may be substituted, generally with serine, to improve the oxidative stability of the molecule and prevent aberrant crosslinking. Conversely, cysteine bond(s) may be added to the antibody or polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

G. Modifications of Antibodies and Polypeptides

Covalent modifications of antibodies and polypeptides are included within the scope of this invention. One type of covalent modification includes reacting targeted amino acid residues of an antibody or polypeptide with an organic derivatizing agent that is capable of reacting with selected side chains or the N- or C-terminal residues of the antibody or polypeptide. Derivatization with bifunctional-agents is useful, for instance, for crosslinking antibody or polypeptide to a water-insoluble support matrix or surface for use in the method for purifying antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimnidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the antibody or polypeptide included within the scope of this invention comprises altering the native glycosylation pattern of the antibody or polypeptide. "Altering the native glycosylation pattern" is intended for purposes herein to mean deleting one or more carbohydrate moieties found in native sequence antibody or polypeptide (either by removing the underlying glycosylation site or by deleting the glycosylation by chemical and/or enzymatic means), and/or adding one or more glycosylation sites that are not present in the native sequence antibody or polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody or polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody or polypeptide (for 0-linked glycosylation sites). The antibody or polypeptide amino acid sequence may optionally be altered through changes at the DNA level, particularly by mutating the DNA encoding the antibody or polypeptide at preselected bases such that codons are generated that will translate into the desired amino acids.

Another means of increasing the number of carbohydrate moieties on the antibody or polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the antibody or polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of antibody or polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

The antibody or polypeptide of the present invention may also be modified in a way to form chimeric molecules comprising an antibody or polypeptide fused to another, heterologous polypeptide or amino acid sequence.

In one embodiment, such a chimeric molecule comprises a fusion of the antibody or polypeptide with a tag polypeptide which provides an epitope to which an anti-tag antibody can selectively bind. The epitope tag is generally placed at the amino- or carboxyl-terminus of the antibody or polypeptide. The presence of such epitope-tagged forms of the antibody or polypeptide can be detected using an antibody against the tag polypeptide. Also, provision of the epitope tag enables the antibody or polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the antibody or polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an antibody or polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also US Pat. No. 5,428,130 issued Jun. 27, 1995.

H. Preparation of Antibodies and Polypeptides

The description below relates primarily to production of antibodies and polypeptides by culturing cells transformed or transfected with a vector containing antibody- and polypeptide-encoding nucleic acid. It is, of course, contemplated that alternative methods, which are well known in the art, may be employed to prepare antibodies and polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the antibody or polypeptide may be chemically synthesized separately and combined using chemical or enzymatic methods to produce the desired antibody or polypeptide.

1. Isolation of DNA Encoding Antibody or Polypeptide

DNA encoding antibody or polypeptide may be obtained from a cDNA library prepared from tissue believed to possess the antibody or polypeptide mRNA and to express it at a detectable level. Accordingly, human antibody or polypeptide DNA can be conveniently obtained from a cDNA library prepared from human tissue. The antibody- or polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding antibody or polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are. transfected or transformed with expression or cloning vectors described herein for antibody or polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell-transfection-and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full-length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for antibody- or polypeptide-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus;* *yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula.* A list of specific species that are exemplary of this class of yeasts may be found in C. Anthony, *The Biochemistry of Methylotrophs,* 269 (1982).

Suitable host cells for the expression of glycosylated antibody or polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/ -DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody or polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding antibody or polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the antibody- or polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the antibody- or polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the antibody- or polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding antibody or polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Antibody or polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the antibody or polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antibody or polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody or polypeptide.

Still other methods, vectors, and host cells suitable for adaptation to the synthesis of antibody or polypeptide in recombinant vertebrate cell culture are described in Gething et al., *Nature,* 293:620-625 (1981); Mantei et al., *Nature,* 281:40-46 (1979); EP 117,060; and EP 117,058.

4. Culturing the Host Cells

The host cells used to produce the antibody or polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.*102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence polypeptide or against a synthetic peptide based on the DNA sequence provided herein or against exogenous sequence fused to polypeptide DNA and encoding a specific antibody epitope.

6. Purification of Antibody and Polypeptide

Forms of antibody and polypeptide may be recovered from culture medium or from host cell lysates. If membrane-bound, it can be released from the membrane using a suitable detergent solution (e.g. Triton-X 100) or by enzymatic cleavage. Cells employed in expression of antibody and polypeptide can be disrupted by various physical or chemical means, such as freeze-thaw cycling, sonication, mechanical disruption, or cell lysing agents.

It may be desired to purify antibody and polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the antibody and polypeptide. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular antibody or polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

I. Pharmaceutical Formulations

Therapeutic formulations of the antibodies, binding oligopeptides, binding organic or inorganic small molecules and/or polypeptides used in accordance with the present invention are prepared for storage by mixing the antibody, polypeptide, oligopeptide or organic/inorganic small molecule having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The formulation may comprise the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an antibody, binding oligopeptide, or binding organic or inorganic small molecule, it may be desirable to include in the one formulation, an additional antibody, e.g., a second antibody which binds a different epitope on the same polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

J. Treatment with Antibodies, Binding Oligopeptides and Binding Organic/Inorganic Small Molecules To determine polypeptide (hepsin and/or HGF) expression in the cancer, various detection assays are available. In one embodiment, polypeptide overexpression may be analyzed by immunohistochemistry (IHC). Parrafin embedded tissue sections from a tumor biopsy may be subjected to the IHC assay and accorded a polypeptide staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for polypeptide expression may be characterized as not overexpressing the polypeptide, whereas those tumors with 2+ or 3+ scores may be characterized as overexpressing the polypeptide.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of polypeptide overexpression in the tumor.

Polypeptide overexpression or amplification may be evaluated using an in vivo detection assay, e.g., by administering a molecule (such as an antibody, oligopeptide or organic small molecule) which binds the molecule to be detected and is tagged with a detectable label (e.g., a radioactive isotope or a fluorescent label) and externally scanning the patient for localization of the label.

As described above, the antibodies, oligopeptides and organic small molecules of the invention have various non-therapeutic applications. The antibodies, oligopeptides and organic/inorganic small molecules of the present invention can be useful for staging of polypeptide-expressing cancers (e.g., in radioimaging). The antibodies, oligopeptides and organic small molecules are also useful for purification or immunoprecipitation of polypeptide from cells, for detection and quantitation of polypeptide in vitro, e.g., in an ELISA or a Western blot, to kill and eliminate polypeptide-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Antibody, oligopeptide or organic small molecule therapy may be especially desirable in elderly patients who do not tolerate the toxicity and side effects of chemotherapy well and in metastatic disease where radiation therapy has limited usefulness. The tumor targeting antibodies, oligopeptides and organic/inorganic small molecules of the invention are useful to alleviate polypeptide-expressing cancers upon initial diagnosis of the disease or during relapse. For therapeutic applications, the antibody, oligopeptide or organic/inorganic small molecule can be used alone, or in combination therapy with, e.g., hormones, antiangiogens, or radiolabelled compounds, or with surgery, cryotherapy, and/or radiotherapy. Antibody, oligopeptide or organic/inorganic small molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered antibody, oligopeptide or organic/inorganic small molecule in conjunction with treatment with the one or more of the preceding chemotherapeutic agents. In particular, combination therapy with palictaxel and modified derivatives (see, e.g., EP0600517) is contemplated. The antibody, oligopeptide or organic/inorganic small molecule will be administered with a therapeutically effective dose of the chemotherapeutic agent. In another embodiment, the antibody, oligopeptide or organic/inorganic small molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an antibody, oligopeptide or organic/inorganic small molecule conjugated with a cytotoxic agent is administered to the patient. Preferably, the immunoconjugate bound to the protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The antibodies, oligopeptides, organic/inorganic small molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic small molecule is preferred.

Other therapeutic regimens may be combined with the administration of the antibody, oligopeptide or organic/inorganic small molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the antibody or antibodies, oligopeptides or organic/inorganic small molecules, with administration of an antibody directed against another tumor antigen associated with the particular cancer.

In another embodiment, the therapeutic treatment methods of the present invention involves the combined administration of an antibody (or antibodies), oligopeptides or organic/inorganic small molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic/inorganic small molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the antibody, oligopeptide or organic/inorganic small molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic/inorganic small molecule therapy. Suitable dosages for any of the above co-administered agents are those presently used and may be lowered due to the combined action (synergy) of the agent and antibody, oligopeptide or organic/inorganic small molecule.

For the prevention or treatment of disease, the dosage and mode of administration will be chosen by the physician according to known criteria. The appropriate dosage of antibody, oligopeptide or organic/inorganic small molecule will depend on the type of disease to be treated, as defined above, the severity and course of the disease, whether the antibody, oligopeptide or organic/inorganic small molecule is administered for preventive or therapeutic purposes, previous therapy, the patient's clinical history and response to the antibody, oligopeptide or organic/inorganic small molecule, and the discretion of the attending physician. The antibody, oligopeptide or organic/inorganic small molecule is suitably administered to the patient at one time or over a series of treatments. Preferably, the antibody, oligopeptide or organic/inorganic small molecule is administered by intravenous infusion or by subcutaneous injections. Depending on the type and severity of the disease, about 1 µg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the antibody. However, other dosage regimens may be useful. A typical daily dosage might range from about 1

µg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

The antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present antibodies of the invention are also contemplated, specifically including the in vivo tumor targeting and any cell proliferation inhibition or cytotoxic characteristics.

Methods of producing the above antibodies are described in detail herein.

The present antibodies, oligopeptides and organic/inorganic small molecules are useful for treating a hepsin and/or HGF-expressing cancer, or alleviating one or more symptoms of the cancer in a mammal. Methods of the invention encompass usage of antagonists in the treatment and/or alleviation of symptoms of metastatic tumors associated with these cancers. The antibody, oligopeptide or organic/inorganic small molecule antagonist is able to bind to at least a portion of the cancer cells that express the polypeptide(s) (hepsin and/or HGF) in the mammal. In one embodiment, the antibody, oligopeptide or organic/inorganic small molecule is effective to destroy or kill polypeptide-expressing and/or -responsive tumor cells or inhibit the growth of such tumor cells, in vitro or in vivo, upon binding to the polypeptide. Such an antibody includes a naked antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an antibody by, e.g., conjugating the antibody with a cytotoxic agent, to form an immunoconjugate as described herein. In some embodiments, the cytotoxic agent or a growth inhibitory agent is a small molecule. In some embodiments, toxins such as calicheamicin or a maytansinoid and analogs or derivatives thereof, are used.

The invention provides a composition comprising an antibody, oligopeptide or organic/inorganic small molecule of the invention, and a carrier. For the purposes of treating cancer, compositions can be administered to the patient in need of such treatment, wherein the composition can comprise one or more antibodies present as an immunoconjugate or as the naked antibody. In a further embodiment, the compositions can comprise these antibodies, oligopeptides or organic/inorganic small molecules in combination with other therapeutic agents such as cytotoxic or growth inhibitory agents, including chemotherapeutic agents. The invention also provides formulations comprising an antibody, oligopeptide or organic/inorganic small molecule of the invention, and a carrier. In one embodiment, the formulation is a therapeutic formulation comprising a pharmaceutically acceptable carrier.

Another aspect of the invention is isolated nucleic acids encoding the antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a cancer or alleviating one or more symptoms of the cancer in a mammal, comprising administering a therapeutically effective amount of an antibody, oligopeptide or organic/inorganic small molecule to the mammal. The antibody, oligopeptide or organic/inorganic small molecule therapeutic compositions can be administered short term (acute) or chronic, or intermittent as directed by physician. Also provided are methods of inhibiting the growth of, and killing a polypeptide (hepsin and/or HGF)-expressing and/or -responsive cell.

The invention also provides kits and articles of manufacture comprising at least one antibody, oligopeptide or organic/inorganic small molecule. Kits containing antibodies, oligopeptides or organic/inorganic small molecules find use, e.g., for cell killing assays, for purification or immunoprecipitation of polypeptide from cells. For example, for isolation and purification of a polypeptide, the kit can contain an antibody, oligopeptide or organic/inorganic small molecule coupled to beads (e.g., sepharose beads). Kits can be provided which contain the antibodies, oligopeptides or organic/inorganic small molecules for detection and quantitation of a polypeptide in vitro, e.g., in an ELISA or a Western blot. Such antibody, oligopeptide or organic/inorganic small molecule useful for detection may be provided with a label such as a fluorescent or radiolabel.

K. Articles of Manufacture and Kits

Another embodiment of the invention is an article of manufacture containing materials useful for the treatment of a polypeptide (hepsin and/or HGF) expressing cancer, such as prostate and ovarian cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an antibody, oligopeptide or organic/inorganic small molecule of the invention. The label or package insert indicates that the composition is used for treating cancer. The label or package insert will further comprise instructions for administering the antibody, oligopeptide or organic/inorganic small molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for polypeptide-expressing or cell killing assays, for purification or immunoprecipitation of a polypeptide from cells. For isolation and purification of a polypeptide, the kit can contain an antibody, oligopeptide or organic/inorganic small molecule coupled to beads (e.g., sepharose beads). Kits can be provided which contain the antibodies, oligopeptides or organic/inorganic small molecules for detection and quantitation of a polypeptide in vitro, e.g., in an ELISA or a Western blot. As with the article of manufacture, the kit comprises a container and a label or package insert on or associated with the container. The container holds a composition comprising at least one antibody, oligopeptide or organic/inorganic small molecule of the invention. Additional containers may be included that contain, e.g., diluents and buffers, control antibodies. The label or package insert may provide a description of the composition as well as instructions for the intended in vitro or detection use.

L. Polypeptides and Polypeptide-Encoding Nucleic Acids—Specific Forms and Applications Nucleotide sequences (or their complement) encoding polypeptides of the invention have various applications in the art of molecular biology, as well as uses for therapy, etc. Polypeptide-encoding nucleic acid will also be useful for the preparation of polypeptides by the recombinant techniques described herein, wherein those polypeptides may find use, for example, in the preparation of antibodies as described herein.

A full-length native sequence polypeptide gene, or portions thereof, may be used as hybridization probes for a cDNA library to isolate other cDNAs (for instance, those encoding naturally-occurring variants of a polypeptide or a polypeptide from other species) which have a desired sequence identity to a native polypeptide sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence polypeptide. By way of example, a screening method will comprise isolating the coding region of the polypeptide gene using the known DNA sequence to synthesize a selected probe of about 40 bases. Hybridization probes may be labeled by a variety of labels, including radionucleotides such as $^{32}$P or $^{35}$S, or enzymatic labels such as alkaline phosphatase coupled to the probe via avidinfbiotin coupling systems. Labeled probes having a sequence complementary to that of the polypeptide gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the polypeptide-encoding nucleic acids include antisense or sense oligonucleotides comprising a singe-stranded nucleic acid sequence (either RNA or DNA) capable of binding to target a polypeptide mRNA (sense) or a polypeptide DNA (antisense) sequence. Antisense or sense oligonucleotides, according to the present invention, comprise a fragment of the coding region of a DNA encoding hepsin, pro-HGF or binding fragments as described herein. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of a protein, wherein the protein may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TAA, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of a polypeptide include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most-internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkeynyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)$.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne ($-CH_2-$)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C\equiv C-CH_3$ or $-CH_2-C\equiv CH$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineening, pages 858-859, Kroschwitz, J. I. ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828, 979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite strucnticres of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—$(CH_2)_2$—O—$CH_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521, 291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example; $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related polypeptide coding sequences.

Nucleotide sequences encoding a polypeptide can also be used to construct hybridization probes for mapping the gene which encodes that polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

The polypeptide can be used in assays to identify other proteins or molecules involved in a binding interaction with the polypeptide. By such methods, inhibitors of the receptor/ligand binding interaction can be identified. Proteins involved in such binding interactions can also be used to screen for peptide or small molecule inhibitors of the binding interaction. Screening assays can be designed to find lead compounds that mimic the biological activity of a native polypeptide or a receptor for the polypeptide. Such screening assays will include assays amenable to high-throughput screening of chemical libraries, making them particularly suitable for identifyjing small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode a polypeptide or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a polypeptide can be used to clone genomic DNA encoding the polypeptide in accordance with established techniques and the genomic sequences used to generate transgenic animals that contain cells which express DNA encoding the polypeptide. Methods for generating transgenic animals, particularly animals such as mice or rats, have become conventional in the art and are described, for example, in U.S. Pat. Nos. 4,736,866 and 4,870,009. Typically, particular cells would be targeted for polypeptide transgene incorporation with tissue-specific enhancers. Transgenic animals that include a copy of a transgene encoding a polypeptide introduced into the germ line of the animal at an embryonic stage can be used to examine the effect of increased expression of DNA encoding a polypeptide. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of a polypeptide can be used to construct a gene "knock out" animal which has a defective or altered gene encoding the polypeptide as a result of homologous recombination between the endogenous gene encoding the polypeptide and altered genomic DNA encoding the polypeptide introduced into an embryonic stem cell of the animal. For example, cDNA encoding the polypeptide can be used to clone genomic DNA encoding the polypeptide in accordance with established techniques. A portion of the cenomic DNA encoding the polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

Nucleic acid encoding the polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The nucleic acid molecules encoding the polypeptides or fragments thereof described herein are useful for chromosome identification. In this regard, there exists an ongoing need to identify new chromosome. markers, since relatively few chromosome marking reagents, based upon actual sequence data are presently available. Each nucleic acid molecule of the present invention can be used as a chromosome marker.

Polypeptides and nucleic acid molecules of the invention may be used diagnostically for tissue typing, wherein the polypeptides may be differentially expressed in one tissue as compared to another, preferably in a diseased tissue as compared to a normal tissue of the same tissue type. Nucleic acid molecules will find use for generating probes for PCR, Northern analysis, Southern analysis and Western analysis.

This invention encompasses methods of screening compounds to identify those that prevent the effect of the polypeptide (antagonists). Screening assays for antagonist drug candidates are designed to identify compounds that bind or complex with the polypeptides encoded by the genes identified herein, or otherwise interfere with the interaction of the encoded polypeptides with other cellular proteins, including e.g., inhibiting the expression of the polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide or the drug candidate is immobilized on a solid phase, e.g., on a microtiter plate, by covalent or non-covalent attachments. Non-covaient attachment gencrally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a polypeptide, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may he added to a third reaction mixture, to serve as positive control. The binding (complex formation) between the test compound and the intra or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the polypeptide may be added to a cell along with the compound to be screened for a particular activity and the ability of the compound to inhibit the activity of interest in the presence of the polypeptide indicates that the compound is an antagonist to the polypeptide. Alternatively, antagonists may be detected by combining the polypeptide and a potential antagonist with membrane-bound polypeptide receptors or encoded receptors under appropriate conditions for a competitive inhibition assay. The polypeptide can be labeled, such as by radioactivity, such that the number of polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.*, 1(2): Chapter 5 (1991). Preferably, expression cloning is employed wherein polyadenylated RNA is prepared from a cell responsive to the polypeptide and a cDNA library created from this RNA is divided into pools and used to transfect COS cells or other cells that are not responsive to the polypeptide. Transfected cells that are grown on glass slides are exposed to labeled polypeptide. The polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro- sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled polypeptide in the presence of the candidate compound. The ability of the compound to enhance or block this interaction could then be measured.

Miore specific examples of potentia 1 antagonists include an oligonucleotide that binds to the fusions of immunoglobulin with a polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the polypeptide that recognizes the receptor but imparts no effect, thereby competitively inhibiting the action of the polypeptide.

Another potential antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides herein, can be used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al., *Science*, 241: 456 (1988); Dervan et al., *Science*, 251:1360 (1991)), thereby preventing transcription and the production of the polypeptide. The antisense RNA oligonucleotide hybridizes to the mRNA in vivo and blocks translation of the mRNA molecule into the polypeptide (antisense—Okano, *Neurochem.*, 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the polypeptide, thereby blocking the normal biological activity of the polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated polypeptide-encoding nucleic acid can be used for recombinantly producing polypeptide using techniques well known in the art and as described herein. In turn, the produced polypeptides can be employed for generating antibodies using techniques well known in the art and as described herein.

Antibodies specifically binding a polypeptide identified herein, as well as other molecules identified by the screening assays disclosed hereinbefore, can be administered for the treatment of various disorders, including cancer, in the form of pharmaceutical compositions.

If the polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/ or produced by recombinant DNA technology. See, e.g., Marasco et al., *Proc. Natl. Acad. Sci. USA*, 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

EXAMPLES

Reagents

The chromogenic substrate S2366 was obtained from DiaPharma Group, Inc. (West Chester, Ohio), Lys-plasminogen from Haematologic Technologies Inc. (Essex Junction, Vt.) and tissue-type plasminogen activator (t-PA) from Genentech, Inc. (South San Francisco, Calif.). Pro-HGF, expressed in Chinese hamster ovary (CHO) cells in the absence of serum and purified by HiTrap Sepharose SP chromatography, was provided by David Kahn (Genentech). HGFA comprising residues Val373-Arg407 was expressed in a baculovirus expression system and purified as described (34). Purified human recombinant FVII, expressed in human 293 cells, was a gift from Mark O'Connell (Genentech) and was described recently (42). Dioleoyl 1,2-diacyl-sn-glycero-3-(phospho-L-serine) (PS) and oleoyl 1,2-diacyl-sn-glycero-3-phosphocholine (PC) (Avanti Polar Lipids Inc., Alabaster, Ala.) were used to produce PCPS vesicles (7:3 molar ratio) essentially as described (43). The molecular weight markers were SeeBlue Plus2 and MultiMark standards (Invitrogen, Carlsbad, Calif.).

Expression and Purification of Hepsin

The cDNA of full length hepsin, obtained from the I.M.A.G.E. consortium (ATCC, Manassas, Va.), was digested with restriction endonucleases EcoRI and Not I (New England Biolabs Inc. Beverly, Mass.) and inserted in the eukaryotic expression vector pRK5E. A secreted His-tagged hepsin cDNA was constructed by fusion of the cDNA coding for the signal sequence of human HGF (amino acids Met1-Gly31) with the cDNA coding for the extracellular domain of human hepsin (Arg45-Leu417: numbering system in accordance with Somoza et al., 2003 (5)). In addition, a $His_8$ tag was added to the C-terminus after Leu417 and the final cDNA construct inserted in the eukaryotic expression vector pCMV.PD5. Hepsin was expressed in a Chinese hamster ovary (CHO) cell transient expression system and purified by nickel-nitrilotriacetic acid (Ni—NTA) affinity chromatography essentially as described for the production of wildtype sHAI-1B (34).

Expression and Purification of sHAI-1B, sHAI-1B Mutants and sHAI-2

A soluble form of HAI-1B (sHAI-1B) comprising the entire extracellular domain was produced in a CHO cell transient expression system and purified as described previously (34). Using site-directed mutagenesis, the $P_1$ residues of KD1 (Arg260) and KD2 (Lys401) were individually changed to Ala and the resulting proteins, sHAI-1B(R260A) and sHAI-1B(K401A), expressed and purified as described (34).

Full length HAI-2 was obtained from a cDNA library derived from human fetal lung RNA (BD Biosciences Clontech, Palto Alto, Calif.) using oligo dT/Not I site as a primer and adapator with Sal I site for the second strand. The cDNA was digested with Sal I and Not I; cDNAs greater than 2.8 kb were ligated to pRK5D. Single stranded DNA of the human lung cDNA/pRK5D library was generated using standard molecular biology methods. Reverse primer (5'-TTTCT-TGAGGCACTCCTCCTTG-3') was annealed to the single-stranded cDNA pool and extended using T7 or T4 DNA polymerase. E. coli were transformed with the synthesized double-stranded DNA and colonies were screened using standard filter hybridization methods. The insert size was analyzed by PCR and restriction endonuclease digestion, XbaI. HAI-2 full length clones were identified and confirmed by DNA sequencing. A soluble form of HAI-2 (sHAI-2) was produced by constructing a cDNA coding for the extracellular domain (Ala28-Lys197; numbering system in accordance with Kawaguchi et al., 1997 (39)) of HAI-2 and addition of a C-terminal $His_8$ tag with a Gly spacer. The obtained cDNA was then inserted into a baculovirus expression vector derived from pVL1393 (BD-Biosciences Pharmingen, San Diego, Calif.). sHAI-2 was expressed in a baculovirus expression system and purified by Ni—NTA affinity chromatography essentially as described for the production of HGF β-chain (44). Protein concentrations were determined by quantitative amino acid analysis.

FVII and Plasminogen Activation Assays

FVII at a concentration of 0.11 mg/ml was activated by 230 nM hepsin in 30 mM Tris-HCl, pH 8.4, 30 mM imidazole, 200 mM NaCl (Tris buffer) in the presence of 0.5 mM PCPS vesicles and 5 mM $CaCl_2$ at 37° C. Reaction aliquots taken at different time points were analyzed by SDS-PAGE (reducing conditions) using a 4-20% gradient gel (Invitrogen, Carlsbad, Calif.). Gels were stained with Simply Blue Safe Stain (Invitrogen).

Plasminogen at 0.12 mg/ml was incubated with 40 nM hepsin or 40 nM t-PA (positive control) in 20 mM Hepes pH 7.5, 150 mM NaCl (Hepes buffer) at 37° C. Reaction aliquots taken at different time points were analyzed by SDS-PAGE as described for FVII activation assays.

Pro-HGF Activation by Hepsin and HGFA

Pro-HGF (0.3 mg/ml) was incubated in Hepes buffer with 40 nM hepsin or with 40 nM HGFA for 4 h at 37° C. and stored at −20° C. until further use. Analysis of the digested material, $HGF_{hepsin}$ and $HGF_{HGFA}$, by SDS-PAGE indicated that >95% of pro-HGF was converted into two-chain HGF.

Pro-HGF activation assays and $^{125}I$-labeling of pro-HGF was carried out as described (34,45). Briefly, $^{125}I$-labeled pro-HGF at 0.05 mg/ml in Hepes buffer was incubated with increasing concentrations (0.16-40 nM) of hepsin or HGFA at 37° C. After 4 h, aliquots were removed and analyzed by SDS-PAGE (4-20% gradient gel) (Invitrogen Corp., Carlsbad, Calif.). For inhibition studies, hepsin (15 nM) was incubated in Hepes buffer with 1 μM of sHAI-1B, sHAI-1B (K401A), sHAI-1B(R260A), or sHAI-2 at 37° C. After 4 h the samples were analyzed by SDS-PAGE and stained with Simply Blue Safe Stain (Invitrogen).

Enzyme Inhibition Assays

Assay conditions were similar to those described by Somoza et al. 2003 (5) using the chromogenic substrate S2366 (L-pyroglutamyl-L-prolyl-L-arginine-p-nitroaniline hydrochloride). Hepsin (final concentration of 0.4 nM) was incubated with increasing concentrations of inhibitors in Tris buffer for 30 min at room temperature. Substrate S2366 was added and the change in absorbance at 405 nm measured on a kinetic microplate reader (Molecular Devices, Sunnyvale Calif.). The concentrations of hepsin and S2366 in this final reaction mixture were 0.4 nM and 0.2 mM (determined $K_m$=0.2 mM), respectively. Inhibitory activities were expressed as fractional activity ($v_i/v_0$) of uninhibited enzyme activity. The inhibitor concentrations giving 50% inhibition ($IC_{50}$) were calculated by fitting the data to a four parameter regression curve fitting program (Kaleidagraph, Synergy Software, Reading, Pa.). At least three independent experiments were performed for each inhibitor.

Cell Proliferation and Migration Assays

Proliferation assays were carried out with the human pancreatic adenocarcinoma cell line BxPC3 obtained from the European Collection of Cell Cultures (CAMR, Centre for Applied Microbiology and Research, Salisbury, Wiltshire, UK). Cells were grown in RPMI medium containing 10% FCS (Sigma, St. Louis, Mo.), 10 mM hepes, 2 mM glutamine, Penicillin-Streptomycin (Invitrogen, Carlsbad, Calif.) and 250 µg/ml G418 (Invitrogen). Confluent cell layers were washed with PBS followed by 10 mM EDTA/PBS and were detached after incubation with trypsin. The cells were resuspended in growth medium and seeded (10,000-15,000 cells/well) into 96-well white bottom MT plates (Cultur Plate™, Packard/PerkinElmer, Boston, Mass.). After 24 h, the growth medium was replaced with RPMI-0.1% BSA. After an additional 24 h, the medium was removed and various concentrations of $HGF_{hepsin}$ and $HGF_{HGFA}$ in RPMI-0.1% BSA were added and the cells were allowed to grow for 72 h. Cell proliferation was then quantified by use of the CellTiter-Glo Luminescent Kit (Promega, Madison, Wis.) according to manufacturer's instructions. Luminsescence was measured on a Tropix TR717 microplate luminometer (Berthold 75323, Bad Wildbad, Germany). After subtraction of background values (proliferation in the absence of HGF), the activities of $HGF_{hepsin}$ and $HGF_{HGFA}$ were expressed as percent of BxPC3 proliferation by 100 ng/ml of an HGF control preparation (obtained from Dr. Ralph Schwall, Genentech).

Cell migration assays with the breast cancer cell line MDA-MB435 (HTB-129, ATCC, Manassas, Va.) were carried out as described (44). Briefly, 0.2 ml of a cell suspension in serum-free medium (0.6-0.8×10$^6$ cells/ml) was added to the upper chambers of 24-well transwell plates (8 µm pore size) (HTS Multiwell™ Insert System, Falcon, Franklin Lakes, N.J.) pre-coated with 10 µg/ml of rat tail collagen Type I (Upstate, Lake Placid, N.Y.). HGF preparations were added to the lower chamber in serum-free medium. After incubation for 13-14 h, cells on the apical side of the membrane were removed and those that migrated to the basal side were fixed in 4% paraformaldehyde followed by staining with a 0.5% crystal violet solution. Cells were solubilized in 10% acetic acid and the $A_{560}$ was measured on a Molecular Devices microplate reader. Pro-migratory activities of HGF mutants were expressed as percent of an HGF control preparation after subtracting basal migration in the absence of HGF.

Met Receptor Phosohorylation Assay

The kinase receptor activation assay (KIRA) was carried out as described (44). Briefly, lung carcinoma A549 cells (CCL-185, ATCC, Manassas, Va.) were seeded in 96 well plates at a density of 50,000 cells per well. After overnight incubation at 37° C., growth medium was removed and cells were serum starved for 30 to 60 min in medium containing 0.1% FBS. Increasing concentrations of $HGF_{hepsin}$ and $HGF_{HGFA}$ in medium containing 0.1% FBS were added. As a control we used an uncleavable single-chain form of HGF (scHGF) in which the cleveage site was mutated (Arg494Glu) (44). After 10 min incubation at 37° C., medium was removed and cells lysed with lysis buffer (Cell Signaling Technologies, Beverly, Mass.) supplemented with protease inhibitor cocktail. The BV-TAG-labeled 4G10 antibody and biotinylated anti-Met antibody were added to the cell lysates. After incubation for 1.5 to 2 h, streptavidin magnetic beads (Dynabeads, Bio Veris) were added and incubated for 45 min. The beads with bound material (anti-Met antibody/Met/anti-phosphotyrosine antibody) were captured by an externally applied magnet. After a wash step the chemiluminescent signal generated by the light source was measured as relative luminescent units on a Bio Veris instrument. For each experiment, the Met phosphorylation by $HGF_{hepsin}$, $HGF_{HGFA}$ or scHGF was expressed as percent of the maximal signal obtained with an HGF control preparation.

Results

Proteolytic Processing of pro-HGF by Hepsin

A soluble form of hepsin encompassing the entire extracellular domain (Arg45-Leu417; numbering system in accordance with Somoza et al., 2003 (5)) and a C-terminal $His_8$ tag was expressed in CHO cells. During the purification process hepsin zymogen spontaneously converted into its two-chain form (FIG. 1A), most likely due to an auto-activation (4). N-terminal sequencing of the ~30 kDa protease domain ($^{163}$IVGGRDTSLGR$^{173}$) confirmed cleavage at the expected Arg162-Ile163 peptide bond rendering the active enzyme. Hepsin actively converted FVII zymogen into two-chain FVIIa (FIG. 1B), consistent with experiments reported by Kazama et al., 1995 (9) using cell surface expressed hepsin to determine FVII activation. Hepsin activity towards pro-HGF was examined by measuring the conversion of $^{125}$I-labelled pro-HGF into two-chain HGF. The results showed that pro-HGF was cleaved by hepsin in a concentration-dependent fashion (FIG. 2A). Hepsin activity was comparable to that of HGFA (FIG. 2B), both enzymes achieving complete conversion of pro-HGF at a concentration of 4-13 nM. In the same assay system, the pro-HGF activators factor XIa, factor XIIa and plasma kallikrein require about 5-6 fold higher concentrations for complete pro-HGF conversion (45). N-terminal sequencing of the ~36k Da and ~39 kDa HGF β-chains gave identical sequences ($^{495}$VVNGIPTRTNIG$^{506}$), showing that hepsin processed pro-HGF at the expected Arg494-Val495 peptide bond. Unlike factor XIa and plasma kallikrein, hepsin did not produce the HGF α2-chain fragment (by cleavage between Arg424-His425) (45), even after prolonged reaction periods. Moreover, hepsin (40 nM) completely lacked the ability to activate plasminogen during a 5 h reaction (FIG. 2C). In comparison, t-PA efficiently processed plasminogen with about 50% of zymogen already cleaved after 0.5 h (FIG. 2C).

Biological Activity of HGF Generated by Hepsin Digestion

Unlabelled pro-HGF (0.3 mg/ml) was completely converted (>95%) into HGF with 40 nM hepsin or with 40 nM HGFA (FIG. 3A) to give $HGF_{hepsin}$ and $HGF_{HGFA}$, respectively. In a kinase receptor assay (KIRA) with A549 lung carcinoma cells, both HGF preparations induced similar concentration-dependent increases in Met phosphorylation, reaching maximal activity at 250 ng/ml (FIG. 3B). As shown previously (44), an uncleavable single chain form of HGF (scHGF) with a changed cleavage site (R494E) had no activity (FIG. 3B). Control experiments showed that hepsin or HGFA alone had no effect (data not shown). Furthermore, $HGF_{hepsin}$ efficiently promoted proliferation of BxPC3 pancreatic cancer cells. The activity was comparable to that of $HGF_{HGFA}$ in the examined range of 5-100 ng/ml (FIG. 4A). Similar results were obtained in a cell migration assay with MDA-MB435 cells using a collagen-coated transwell migration system. As found in cell proliferation assays, the pro-migratory effects of $HGF_{hepsin}$ were concentration-dependent and indistinguishable from the activity of $HGF_{HGFA}$ (FIG. 4B).

Inhibition of Hepsin Enzymatic Activity by sHAI-1B and sHAI-2

An initial screen of 26 commercially available chromogenic substrates showed that S2366, a substrate reported by Somoza et al., 2003 (5), was hydrolyzed by hepsin at the highest rate (data not shown). Using S2366 as a substrate, the inhibitory activities of highly purified, soluble forms of wild-type HAI-1B (sHAI-1B) and HAI-2 (sHAI-2) were measured. In addition, we produced the two sHAI-1B mutants sHAI-1B(R260A) and sHAI-1B(K401A) in which the individual Kunitz domains were inactivated by replacing the $P_1$ residues (Arg260 in KD1 and Lys401 in KD2) with alanine (34). The results showed that both sHAI-1B and sHAI-2 potently inhibited hepsin enzymatic activity with $IC_{50}$ values of 21.1±2.7 nM and 1.3±0.3 nM, respectively (FIG. 5). Moreover, mutant sHAI-1B(K401A) containing a non-functional KD2 was equally potent as wildtype sHAI-1B, whereas sHAI-1B(R260A) had >47-fold reduced activity (FIG. 5). The obtained $IC_{50}$ values are summarized in Table 1.

TABLE 1

Inhibition of hepsin by Kunitz domain inhibitors

| Inhibitors | $IC_{50}$ (nM) |
| --- | --- |
| sHAI-1B wt | 21.1 ± 2.7 |
| sHAI-1B(K401A) | 18.2 ± 3.7 |
| sHAI-1B(R260A) | >1000 |
| sHAI-2 | 1.3 ± 0.3 |

Inhibition of Hepsin-Mediated Pro-HGF Activation

The ability of sHAI-1B and sHAI-2 to interfere with macromolecular substrate processing was measured in a $^{25}$I-pro-HGF activation assay. The results obtained were in full agreement with their inhibitory activities determined in amidolytic assays. At concentrations of 1 μM sHAI-2, wildtype sHAI-1B and sHAI-1B(K401A), there was complete inhibition of pro-HGF cleavage (FIG. 6). In contrast, 1 μM sHAI-1B(R260A) showed no inhibition and pro-HGF activation proceeded to complete conversion (FIG. 6).

Discussion

The HGF/Met signaling pathway plays an important role in human physiology and pathology, including tumor invasion and metastasis. The local availability of active HGF is controlled by chymotrypsin-like serine proteases and their cognate inhibitors, which regulate processing of inactive pro-HGF in the extracellular environment. Therefore, perturbations of this 'upstream' pro-HGF convertase pathway in cancer may promote tumor growth by accelerating pro-HGF processing. Here, we demonstrate that hepsin, a serine protease highly upregulated in prostate and ovarian cancer, is a potent activator of pro-HGF. Thus, hepsin likely plays an important role in effecting tumor growth by activatinig the HGF/Met signaling pathway, which has been implicated in prostate (46-48) as well as ovarian cancer (49,50).

Hepsin proteolytically cleaved pro-HGF at the Arg494-Val495 peptide bond without any additional cleavage at Arg424-His425 in Kringle domain 4, a site recognized by factor XIa and plasma kallikrein (45). The two-chain HGF generated by hepsin was fully functional, inducing Met receptor phosphorylation and promoting cell proliferation and migration with activities comparable to HGF generated by HGFA. The molecular mechanism underlying the hepsin-mediated conversion of inactive pro-HGF into an active growth factor has similarity to the proteolytic zymogen to enzyme conversion of chymotrypsin-like serine proteases.

This is supported by recent studies on the structural consequences of pro-HGF activation, demonstrating that cleavage at Arg494-Val495 leads to conformational changes in the protease-like HGF β-chain and the full maturation of a Met receptor binding site (44,51). This Met binding site, which is centered on the 'active site region' and 'activation domain' of HGF, bears remarkable resemblance to the substrate processing region of serine proteases (44,51). Thus, pro-HGF cleavage by hepsin effects structural rearrangements on HGF β that allow the formation of productive HGF/Met signaling complexes. The proteolytic activity of hepsin towards pro-HGF appears highly specific, since it did not cleave plasminogen, the closest structural homolog of pro-HGF. Hepsin had no proteolytic activity towards other serine protease substrates, such as prothrombin, protein C, factor X and factor IX (9).

Studies with HGF null mice show that the HGF/Met pathway is essential for normal embryonic development and survival (52,53). In contrast, mice deficient in the hepsin gene develop normally, indicating that hepsin is unlikely the main HGF activator during embryogenesis. Similar to hepsin, deficiencies of the other known pro-HGF convertases matriptase (54), factor XI (55), prekallikrein (56) and u-PA (57) are not embryonic lethal. Because of its importance in embryogenesis and post-natal physiology, HGF activity may be regulated in a concerted manner by multiple pro-HGF convertase systems. If so, combined pro-HGF convertase gene deficiencies should result in developmental defects similar to HGF null mice. Alternatively, the pro-HGF convertase regulating HGF processing during embryogenesis may not yet have been identified.

HAI-1B, HAI-1 and HAI-2 are epithelial cell surface inhibitors and are expressed in many normal tissues and in tumors (34,58-63). As such, they are ideally located to regulate the enzymatic activity of epithelial cell expressed TTSPs and possibly other cell surface associated serine proteases. Indeed, the HAI-1 splice variants HAI-1 and HAI-1B potently inhibit the TTSP matriptase (MT-SP1) and complexes of HAI-1 with matriptase have been found in human breast milk (38). Here, we demonstrate that both sHAI-1B and sHAI-2 are also potent inhibitors of hepsin enzymatic activity. Moreover, $P_1$ residue-directed mutagenesis experiments demonstrated that inhibition of hepsin is entirely mediated by KD1 of sHAI-B, since the mutant sHAI-1B(R260A) was inactive in pro-HGF assays and had <1% of wildtype and KD2 mutant activity in amidolytic assays. Thus, hepsin, matriptase and HGFA not only have comparable pro-HGF converting activities (34) but are also inhibited by sHAI-1B with equal potencies (16-30 nM) in a KD1-specific fashion (34,64). The splice variants HAI-1 and HAI-1B only differ by the absence or presence of 16 amino acids located C-terminal to KD1. Their expression pattern in tissues, including prostate and ovarian tumors, is identical and so far no significant differences in potency and target protease pattern have been found. Therefore, we consider the in vivo functions of the two splice variants as equivalent. The role of HAI 2 Kunitz domains was not specifically addressed in our study. For most of its target enzymes, HAI-2 utilizes both the N-and C-terminal Kunitz domains (41,65).

The functional association of hepsin with HAI-1B and HAI-2 in vitro together with their localization to epithelial cell surfaces in vivo suggests that they may constitute a physiologically relevant enzyme-inhibitor system. For example, the two HAI-1 splice variants and HAI-2 are expressed in normal prostate and prostate cancer cell lines (34,59,61) and HAI-1 antigen was localized to the secretory cell layer of prostate glandular epithelium (59). Intriguingly, hepsin expression in prostate tumors was localized to the same epithelial compartment (19,20), supporting the idea that HAI-1 and possibly HAI-2 associate with hepsin in vivo. While hepsin expression is strongly upregulated in prostate cancer (17-22), HAI-1 and HAI-2 increase only slightly (about 1.5-fold) according to gene expression results reported by Welsh et al., 2001 (17). As a consequence, hepsin enzymatic activity in tumors may be inadequately controlled and could lead to enhanced pro-HGF processing and tumor progression. Similar imbalances of pro-HGF convertase/inhibitor systems have been described for matriptase/HAI-1 in ovarian cancer (62, 63), HGFA/HAI-1 in colorectal cancer (66,67) and HGFA/HAI-1 in renal cell carcinoma (68). The upregulated expression of hepsin in some of these cancers suggests that certain convertase/inhibitor systems comprise multiple enzymes and therefore increased enzyme/inhibitor ratios could magnify the consequences for malignancy.

In conclusion, the results presented show that hepsin efficiently activates pro-HGF, thus revealing a functional link between hepsin on the tumor epithelial surface and the extracellular matrix containing inactive growth factor precursor. The finding that HAI-1B and HAI-2 are potent inhibitors of hepsin, which is upregulated in prostate and ovarian cancer, provides new approaches for cancer treatment. For example, the functional Kunitz domains of HAI-1B or HAI-2 could serve as scaffolds for generating more specific and/or more potent enzyme inhibitors by use of phage display technology, which has been successfully applied to other Kunitz domain scaffolds (69,70).

Footnotes/Abbreviations $^1$Factor VIIa, FVIIa; Hepes buffer, 20 mM Hepes pH 7.5, 150 mM NaCl; Tris buffer, 30 MM Tris-HCl, pH 8.4, 30 mM imidazole, 200 mM NaCl; pro-HGF, single-chain hepatocyte growth factor, HGF, two-chain hepatocyte growth factor; HGFA hepatocyte growth factor activator; HAI-1, hepatocyte growth factor activator inhibitor-1; HAI-1B, a splice variant of hepatocyte growth factor activator inhibitor-1; HAI-2, hepatocyte growth factor activator inhibitor-2; KD1 and KD2, N- and C-terminal Kunitz domain of HAI-1B; sHAI-1B, soluble form of HAI-1B encompassing the extracellular domain; sHAI-2, soluble form of HAI-2 encompassing the extracellular domain; $HGF_{hepsin}$, HGF produced by activation of pro-HGF with hepsin; $HGF_{HGFA}$, HGF produced by activation of pro-HGF with HGFA; scHGF, uncleavable single-chain HGF with a mutated cleavage site (Arg494Glu); u-PA, urokinase-type plasminogen activator; t-PA, tissue-type plasminogen activator. Ni-NTA, nickel-nitrilotriacetic acid.

PARTIAL LIST OF REFERENCES

1. Szabo, R., Wu, Q., Dickson, R. B., Netzel-Arnett, S., Antalis, T. M., and Bugge, T. H. (2003) *Thromb. Haemost.* 90, 185-193
2. Tsuji, A., Torres-Rosado, A., Arai, T., Le Beau, M. M., Lemons, R. S., Chou, S.-H., and Kurachi, K. (1991) *J Biol Chem* 266, 16948-16953
3. Leytus, S. P., Loeb, K. R., Hagen, F. S., Kurachi, K., and Davie, E. W. (1988) *Biochemistry* 27, 1067-1074
4. Vu, T.-K. H., Liu, R. W., Haaksma, C. J., Tomasek, J. J., and Howard, E. W. (1997) *J Biol Chem* 272, 31315-31320
5. Somoza, J. R., Ho, J. D., Luong, C., Ghate, M., Sprengeler, P. A., Mortara, K., Shrader, W. D., Sperandio, D., Chan, H., McGrath, M. E., and Katz, B. A. (2003) *Structure* 11, 1123-1131
6. McCallum, C. D., Hapak, R. C., Neuenschwander, P. F., Morrissey, J. H., and Johnson, A. E. (1996) *J. Biol. Chem.* 271, 28168-28175
7. Mutucumarana, V. P., Duffy, E. J., Lollar, P., and Johnson, A. E. (1992) *J. Biol. Chem.* 267, 17012-17021
8. Husten, E. J., Esmon, C. T., and Johnson, A. E. (1987) *J. Biol. Chem.* 262, 12953-12961
9. Kazama, Y., Hamamoto, T., Foster, D. C., and Kisiel, W. (1995) *J. Biol. Chem.* 270, 66-72
10. Wu, Q., Yu, D., Post, J., Halks-Miller, M., Sadler, J. E., and Morser, J. (1998) *J. Clin. Invest.* 101, 321-326
11. Yu, I.-S., Chen, H.-J., Lee, Y.-S. E., Huang, P.-H., Lin, S.-R., Tsai, T.-W., and Lin, S.-W. (2000) *Thromb. Haemost.* 84, 865-870
12. Zacharski, L. R., Ornstein, D. L., Memoli, V. A., Rousseau, S. M., and Kisiel, W. (1998) *Thromb. Haemost.* 79, 876-877
13. Rapaport, S. I., and Rao, L. V. M. (1995) *Thromb. Haemost.* 74, 7-17
14. Mann, K. G. (1999) *Thromb. Haemost.* 82, 165-174
15. Torres-Rosado, A., O'Shea, K. S., Tsuji, A., Chou, S.-H., and Kurachi, K. (1993) *Proc Natl Acad Sci USA* 90, 7181-7185
16. Srikantan, V., Valladares, M., Rhim, J. S., Moul, J. W., and Srivastava, S. (2002) *Cancer Res.* 62, 6812-6816
17. Welsh, J. B., Sapinoso, L. M., Su, A. I., Kern, S. G., Wang-Rodriguez, J., Moskaluk, C. A., Frierson Jr., H. F., and Hampton, G. M. (2001) *Cancer Res.* 61, 5974-5978
18. Stamey, T. A., Warrington, J. A., Caldwell, M. C., Chen, Z., Fan, Z., Mahadevappa, M., McNeal, J. E., Nolley, R., and Zhang, Z. (2001) *J. Urol.* 166, 2171-2177
19. Magee, J. A., Araki, T., Patil, S., Ehrig, T., True, L., Humphrey, P. A., Catalona, W. J., Watson, M. A., and Milbrandt, J. (2001) *Cancer Res.* 61, 5692-5696
20. Dhanasekaran, S. M., Barrette, T. R., Ghosh, D., Shah, R., Varambally, S., Kurachi, K., Pienta, K. J., Rubin, M. A., and Chinnaiyan, A. M. (2001) *Nature* 412, 822-826
21. Luo, J., Duggan, D. J., Chen, Y., Sauvageot, J., Ewing, C. M., Bittner, M. L., Trent, J. M., and Isaacs, W. B. (2001) *Cancer Res.* 61, 4683-4688
22. Stephan, C., Yousef, G. M., Scorilas, A., Jung, K., Jung, M., Kristiansen, G., Hauptmann, S., Kishi, T., Nakamura, T., Loening, S. A., and Diamandis, E. P. (2004) *J. Urol.* 171, 187-191
23. Tanimoto, H., Yan, Y., Clarke, J., Korourian, S., Shigemasa, K., Parmley, T. H., Parham, G. P., and O'Brien, T. J. (1997) *Cancer Res.* 57, 2884-2887
24. Lin, C.-Y., Anders, J., Johnson, M., Sang, Q. A., and Dickson, R. B. (1999) *J. Biol. Chem.* 274, 18231-18236
25. Takeuchi, T., Shuman, M. A., and Craik, C. S. (1999) *Proc. Natl. Acad. Sci. USA* 96, 11054-11061
26. Birchmeier, C., Birchmeier, W., Gherardi, E., and Vande Woude, G. F. (2003) *Nature Rev. Mol. Cell Biol.* 4, 915-925
27. Trusolino, L., and Comoglio, P. M. (2002) *Nature Rev. Cancer* 2, 289-300
28. Hartmann, G., Naldini, L., Weidner, K. M., Sachs, M., Vigna, E., Comoglio, P. M., and Birchmeier, W. (1992) *Proc. Natl. Acad. Sci. USA* 89, 11574-11578
29. Lokker, N. A., Mark, M. R., Luis, E. A., Bennett, G. L., Robbins, K. A., Baker, J. B., and Godowski, P. J. (1992) *EMBO J* 11, 2503-2510
30. Naka, D., Ishii, T., Yoshiyama, Y., Miyazawa, K., Hara, H., Hishida, T., and Kitamura, N. (1992) *J. Biol. Chem.* 267, 20114-20119
31. Gak, E., Taylor, W. G., Chan, A. M.-L., and Rubin, J. S. (1992) *FEBS Lett.* 311, 17-21
32. Miyazawa, K., Shimomura, T., Kitamura, A., Kondo, J., Morimoto, Y., and Kitamura, N. (1993) *J. Biol. Chem.* 268, 10024-10028

33. Lee, S.-L., Dickson, R. B., and Lin, C.-Y. (2000) *J. Biol. Chem.* 275, 36720-36725
34. Kirchhofer, D., Peek, M., Li, W., Starnos, J., Eigenbrot, C., Kadkhodayan, S., Elliott, J. M., Corpuz, R. T., Lazarus, R. A., and Moran, P. (2003) *J. Biol. Chem.* 278, 36341-36349
35. Naldini, L., Tamagnone, L., Vigna, E., Sachs, M., Hartmann, G., Birchmeier, W., Daikuhara, Y., Tsubouchi, H., Blasi, F., and Comoglio, P. M. (1992) *EMBO J.* 11, 4825-4833
36. Shimomura, T., Miyazawa, K., Komiyama, Y., Hiraoka, H., Naka, D., Morimoto, Y., and Kitamura, N. (1995) *Eur. J. Biochem.* 229, 257-261
37. Shimomura, T., Denda, K., Kitamura, A., Kawaguchi, T., Kito, M., Kondo, J., Kagaya, S., Qin, L., Takata, H., Miyazawa, K., and Kitamura, N. (1997) *J. Biol. Chem.* 272, 6370-6376
38. Lin, C.-Y., Anders, J., Johnson, M., and Dickson, R. B. (1999) *J. Biol. Chem.* 274, 18237-18242
39. Kawaguchi, T., Qin, L., Shimomura, T., Kondo, J., Matsumoto, K., Denda, K., and Kitamura, N. (1997) *J. Biol. Chem.* 272, 27558-27564
40. Marlor, C. W., Delaria, K. A., Davis, G., Muller, D. K., Greve, J. M., and Tamburini, P. P. (1997) *J. Biol. Chem.* 272, 12202-12208
41. Delaria, K. A., Muller, D. K., Marlor, C. W., Brown, J. E., Das, R. C., Roczniak, S. O., and Tamburini, P. P. (1997) *J. Biol. Chem.* 272, 12209-12214
42. Kelley, R. F., Yang, J., Eigenbrot, C., Moran, P., Peek, M., Lipari, M. T., and Kirchhofer, D. (2004) *Biochemistry* 43, 1223-1229
43. Mimms, L. T., Zampighi, G., Nozaki, Y., Tanford, C., and Reynolds, J. A. (1981) *Biochemistry* 20, 833-840
44. Kirchhofer, D., Yao, X., Peek, M., Eigenbrot, C., Lipari, M. T., Billeci, K. L., Maun, H. R., Moran, P., Santell, L., Wiesmann, C., and Lazarus, R. A. (2004) *J. Biol. Chem. (in press)*
45. Peek, M., Moran, P., Mendoza, N., Wickramasinghe, D., and Kirchhofer, D. (2002) *J. Biol. Chem.* 277, 47804-47809
46. Gmyrek, G. A., Walburg, M., Webb, C. P., Yu, H.-M., You, X., Darracott Vaughan, E., Vande Woude, G. F., and Kundsen, B. S. (2001) *Am. J. Pathol.* 159, 579-590
47. Knudsen, B. S., Gmyrek, G. A., Inra, J., Scherr, D. S., Vaughan, E. D., Nanus, D. M., Kattan, M. W., Gerald, W. L., and Vande Woude, G. F. (2002) *Urology* 60, 1113-1117
48. Zhu, X., and Humphrey, P. A. (2000) *Urology* 56, 1071-1074
49. Huntsman, D., Resau, J. H., Klineberg, E., and Auersperg, N. (1999) *Am. J. Pathol.* 155, 343-348
50. Wong, A. S. T., Pelech, S. L., Woo, M. M. M., Yim, G., Rosen, B., Ehien, T., Leung, P. C. K., and Auersperg, N. (2001) *Oncogene* 20, 1318-1328
51. Stamos, J., Lazarus, R. A., Yao, X., Kirchhofer, D., and Wiesmann, C. (2004) *EMBO J.* 23, 2325-2335
52. Schmidt, C., Bladt, F., Goedecke, S., Brinkmann, V., Zschiesche, W., Sharpe, M., Gherardi, E., and Birchmeier, C. (1995) *Nature (London)* 373, 699-702
53. Uehara, Y., Minowa, O., Mori, C., Shiota, K., Kuno, J., Noda, T., and Kitamura, N. (1995) *Nature (London)* 373, 702-705
54. List, K., Haudenschild, C. C., Szabo, R., Chen, W., Wahl, S. M., Swaim, W., Engelholm, L. H., Behrendt, N., and Bugge, T. H. (2002) *Oncogene* 21, 3765-3779
55. Gailani, D., Lasky, N. M., and Broze Jr., G. J. (1997) *Blood Coag. Fibrinol.* 8, 134-144
56. Hathaway, W. E., Wuepper, K. D., Weston, W. L., Humbert, J. R., Rivers, R. P. A., Genton, E., August, C. S., Montgomery, R. R., and Mass, M. F. (1976) *Am. J. Med.* 60, 654-664
57. Carmeliet, P., Schoonjans, L., Kieckens, L., Ream, B., Degen, J., Bronson, R., De Vos, R., van den Oord, J. J., Collen, D., and Mulligan, R. C. (1994) *Nature* 368, 419-424
58. Hamasuna, R., Kataoka, H., Meng, J.-Y., Itoh, H., Moriyama, T., Wakisaka, S., and Koono, M. (2001) *Int. J. Cancer* 93, 339-345
59. Kataoka, H., Suganuma, T., Shimomura, T., Itoh, H., Kitamura, N., Nabeshima, K., and Koono, M. (1999) *J. Histochem. Cytochem.* 47, 673-682
60. Kataoka, H., Itoh, H., Uchino, H., Hamasuna, R., Kitamura, N., Nabeshima, K., and Koono, M. (2000) *Cancer Lett.* 148, 127-134
61. Parr, C., and Jiang, W. G. (2001) *Int. J. Oncol.* 19, 857-863
62. Oberst, M., Anders, J., Xie, B., Singh, B., Ossandon, M., Johnson, M., Dickson, R. B., and Lin, C.-Y. (2001) *Am. J. Pathol.* 158, 1301-1311
63. Oberst, M. D., Johnson, M. D., Dickson, R. B., Lin, C.-Y., Singh, B., Stewart, M., Williams, A., al-Nafussi, A., Smyth, J. F., Gabra, H., and Sellar, G. C. (2002) *Clin. Cancer Res.* 8, 1101-1107
64. Denda, K., Shimomura, T., Kawaguchi, T., Miyazawa, K., and Kitamura, N. (2002) *J. Biol. Chem.* 277, 14053-14059
65. Qin, L., Denda, K., Shimomura, T., Kawaguchi, T., and Kitamura, N. (1998) *FEBS lett.* 436, 111-114
66. Kataoka, H., Hamasuna, R., Itoh, H., Kitamura, N., and Koono, M. (2000) *Cancer Res.* 60, 6148-6159
67. Kataoka, H., Uchino, H., Denda, K., Kitamura, N., Itoh, H., Tsubouchi, H., Nabeshima, K., and Koono, M. (1998) *Cancer Lett.* 128, 219-227
68. Yamauchi, M., Kataoka, H., Itoh, H., Seguchi, T., Hasui, Y., and Osada, Y. (2004) *J. Urol.* 171, 890-896
69. Dennis, M. S., and Lazarus, R. A. (1994) *J. Biol. Chem.* 269, 22129-22136
70. Dennis, M. S., Herzka, A., and Lazarus, R. A. (1995) *J. Biol. Chem.* 270, 25411-25417

We claim:

1. A method of identifying a candidate inhibitor substance that inhibits hepsin activation of HGF, said method comprising:

a) contacting a candidate substance with a first sample comprising hepsin and a pro-HGF substrate, wherein the pro-HGF substrate is a polypeptide comprising pro-HGF or a fragment thereof comprising a wild type form of the R494-V495 peptide linkage and capable of being cleaved by hepsin, wherein the hepsin is a native hepsin or a hepsin variant having at least about 90% identity to a native hepsin and capable of activating pro-HGF, and wherein hepsin in the sample is in an effective amount for activating said pro-HGF substrate, and (b) comparing amount of pro-HGF substrate activation in the sample with amount of pro-HGF substrate activation in a reference sample comprising similar amounts of hepsin and pro-HGF substrate as the first sample but that has not been contacted with said candidate substance, whereby a decrease in amount of pro-HGF substrate activation in the first sample compared to the reference sample indicates that the candidate substance is capable of inhibiting hepsin activation of single chain HGF (pro-HGF).

2. A method of identifying a candidate inhibitor substance that inhibits hepsin activation of HGF, said method comprising:

(a) contacting a candidate substance with a first sample comprising hepsin and a pro-HGF substrate, wherein the pro-HGF substrate comprises a cleavage site of human HGF that fits the consensus cleavage site of proteases wherein the cleavage site comprises basic residue at position P1 and two hydrophobic amino acid residues in positions P1' and P2', wherein the pro-HGF substrate is capable of being cleaved by hepsin, wherein the hepsin is a native hepsin or a hepsin variant having at least about 90% identity to a native hepsin and capable of activating pro-HGF, and wherein hepsin in the sample is in an effective amount for activating said pro-HGF substrate, and (b) comparing amount of pro-HGF substrate activation in the sample with amount of pro-HGF substrate activation in a reference sample comprising similar amounts of hepsin and pro-HGF substrate as the first sample but that has not been contacted with said candidate substance, whereby a decrease in amount of pro-HGF substrate activation in the first sample compared to the reference sample indicates that the candidate substance is capable of inhibiting hepsin activation of single chain HGF (pro-HGF).

3. A method of determining whether a substance inhibits hepsin activation of HGF, said method comprising:

(a) contacting a candidate substance with a first sample comprising hepsin and a pro-HGF substrate, wherein the pro-HGF substrate is a polypeptide comprising pro-HGF or a fragment thereof comprising a wild type form of the R494-V495 peptide linkage and capable of being cleaved by hepsin, wherein the hepsin is a native hepsin or a hepsin variant having at least about 90% identity to a native hepsin and capable of activating pro-HGF, and wherein hepsin in the sample is in an effective amount for activating said pro-HGF substrate, and (b) comparing amount of pro-HGF substrate activation in the sample with amount of pro-HGF substrate activation in a reference sample comprising similar amounts of hepsin and pro-HGF substrate as the first sample but that has not been contacted with said candidate substance, whereby a decrease in amount of pro-HGF substrate activation in the first sample compared to the reference sample indicates that the candidate substance is capable of inhibiting hepsin activation of single chain HGF (pro-HGF).

4. A method of determining whether a substance inhibits hepsin activation of HGF, said method comprising:

(a) contacting a candidate substance with a first sample comprising hepsin and a pro-HGF substrate, wherein the pro-HGF substrate comprises a cleavage site of human HGF that fits the consensus cleavage site of proteases wherein the cleavage site comprises basic residue at position P1 and two hydrophobic amino acid residues in positions P1' and P2', wherein the pro-HGF substrate is capable of being cleaved by hepsin, wherein the hepsin is a native hepsin or a hepsin variant having at least about 90% identity to a native hepsin and capable of activating pro-HGF, and wherein hepsin in the sample is in an effective amount for activating said pro-HGF substrate, and (b) comparing amount of pro-HGF substrate activation in the sample with amount of pro-HGF substrate activation in a reference sample comprising similar amounts of hepsin and pro-HGF substrate as the first sample but that has not been contacted with said candidate substance, whereby a decrease in amount of pro-HGF substrate activation in the first sample compared to the reference sample indicates that the candidate substance is capable of inhibiting hepsin activation of single chain HGF (pro-HGF).

* * * * *

SEQUENCE LISTING

<160> NUMBER OF SEQ ID NOS: 2

<210> SEQ ID NO 1
<211> LENGTH: 417
<212> TYPE: PRT
<213> ORGANISM: Homo sapiens

<400> SEQUENCE: 1

```
Met Ala Gln Lys Glu Gly Gly Arg Thr Val Pro Cys Cys Ser Arg
  1               5                  10                  15

Pro Lys Val Ala Ala Leu Thr Ala Gly Thr Leu Leu Leu Leu Thr
                 20                  25                  30

Ala Ile Gly Ala Ala Ser Trp Ala Ile Val Ala Val Leu Leu Arg
                 35                  40                  45

Ser Asp Gln Glu Pro Leu Tyr Pro Val Gln Val Ser Ser Ala Asp
                 50                  55                  60

Ala Arg Leu Met Val Phe Asp Lys Thr Glu Gly Thr Trp Arg Leu
                 65                  70                  75

Leu Cys Ser Ser Arg Ser Asn Ala Arg Val Ala Gly Leu Ser Cys
                 80                  85                  90

Glu Glu Met Gly Phe Leu Arg Ala Leu Thr His Ser Glu Leu Asp
                 95                 100                 105

Val Arg Thr Ala Gly Ala Asn Gly Thr Ser Gly Phe Phe Cys Val
                110                 115                 120

Asp Glu Gly Arg Leu Pro His Thr Gln Arg Leu Leu Glu Val Ile
                125                 130                 135

Ser Val Cys Asp Cys Pro Arg Gly Arg Phe Leu Ala Ala Ile Cys
                140                 145                 150

Gln Asp Cys Gly Arg Arg Lys Leu Pro Val Asp Arg Ile Val Gly
                155                 160                 165

Gly Arg Asp Thr Ser Leu Gly Arg Trp Pro Trp Gln Val Ser Leu
                170                 175                 180

Arg Tyr Asp Gly Ala His Leu Cys Gly Gly Ser Leu Leu Ser Gly
                185                 190                 195

Asp Trp Val Leu Thr Ala Ala His Cys Phe Pro Glu Arg Asn Arg
                200                 205                 210

Val Leu Ser Arg Trp Arg Val Phe Ala Gly Ala Val Ala Gln Ala
                215                 220                 225

Ser Pro His Gly Leu Gln Leu Gly Val Gln Ala Val Val Tyr His
                230                 235                 240

Gly Gly Tyr Leu Pro Phe Arg Asp Pro Asn Ser Glu Glu Asn Ser
                245                 250                 255

Asn Asp Ile Ala Leu Val His Leu Ser Ser Pro Leu Pro Leu Thr
                260                 265                 270

Glu Tyr Ile Gln Pro Val Cys Leu Pro Ala Ala Gly Gln Ala Leu
                275                 280                 285

Val Asp Gly Lys Ile Cys Thr Val Thr Gly Trp Gly Asn Thr Gln
                290                 295                 300

Tyr Tyr Gly Gln Gln Ala Gly Val Leu Gln Glu Ala Arg Val Pro
                305                 310                 315

Ile Ile Ser Asn Asp Val Cys Asn Gly Ala Asp Phe Tyr Gly Asn
                320                 325                 330

Gln Ile Lys Pro Lys Met Phe Cys Ala Gly Tyr Pro Glu Gly Gly
                335                 340                 345

Ile Asp Ala Cys Gln Gly Asp Ser Gly Gly Pro Phe Val Cys Glu
                350                 355                 360

Asp Ser Ile Ser Arg Thr Pro Arg Trp Arg Leu Cys Gly Ile Val
                365                 370                 375

Ser Trp Gly Thr Gly Cys Ala Leu Ala Gln Lys Pro Gly Val Tyr
                380                 385                 390

Thr Lys Val Ser Asp Phe Arg Glu Trp Ile Phe Gln Ala Ile Lys
```

```
                    395                 400                 405
Thr His Ser Glu Ala Ser Gly Met Val Thr Gln Leu
                410                 415

<210> SEQ ID NO 2
<211> LENGTH: 476
<212> TYPE: PRT
<213> ORGANISM: Homo sapiens

<400> SEQUENCE: 2

Met Ala Gln Lys Glu Gly Gly Arg Thr Val Pro Cys Cys Ser Arg
  1               5                  10                  15

Pro Lys Val Ala Ala Leu Thr Ala Gly Thr Leu Leu Leu Leu Thr
                 20                  25                  30

Ala Ile Gly Ala Ala Ser Trp Ala Ile Val Ala Val Leu Leu Arg
                 35                  40                  45

Ser Asp Gln Glu Pro Leu Tyr Pro Val Gln Val Ser Ser Ala Asp
                 50                  55                  60

Ala Arg Leu Met Val Phe Asp Lys Thr Glu Gly Thr Trp Arg Leu
                 65                  70                  75

Leu Cys Ser Ser Arg Ser Asn Ala Arg Val Ala Gly Leu Ser Cys
                 80                  85                  90

Glu Glu Met Gly Phe Leu Arg Ala Leu Thr His Ser Glu Leu Asp
                 95                 100                 105

Val Arg Thr Ala Gly Ala Asn Gly Thr Ser Gly Phe Phe Cys Val
                110                 115                 120

Asp Glu Gly Arg Leu Pro His Thr Gln Arg Leu Leu Glu Val Ile
                125                 130                 135

Ser Val Cys Asp Cys Pro Arg Gly Arg Phe Leu Ala Ala Ile Cys
                140                 145                 150

Gln Gly Glu Ile Leu Lys Leu Arg Thr Leu Ser Phe Arg Pro Leu
                155                 160                 165

Gly Arg Pro Arg Pro Leu Lys Leu Pro Arg Met Gly Pro Cys Thr
                170                 175                 180

Phe Arg Pro Pro Arg Ala Gly Pro Ser Leu Gly Ser Gly Asp Leu
                185                 190                 195

Gly Ser Ser Pro Leu Ser Pro Pro Ala Asp Pro Cys Pro Thr
                200                 205                 210

Asp Cys Gly Arg Arg Lys Leu Pro Val Asp Arg Ile Val Gly Gly
                215                 220                 225

Arg Asp Thr Ser Leu Gly Arg Trp Pro Trp Gln Val Ser Leu Arg
                230                 235                 240

Tyr Asp Gly Ala His Leu Cys Gly Gly Ser Leu Leu Ser Gly Asp
                245                 250                 255

Trp Val Leu Thr Ala Ala His Cys Phe Pro Glu Arg Asn Arg Val
                260                 265                 270

Leu Ser Arg Trp Arg Val Phe Ala Gly Ala Val Ala Gln Ala Ser
                275                 280                 285

Pro His Gly Leu Gln Leu Gly Val Gln Ala Val Val Tyr His Gly
                290                 295                 300

Gly Tyr Leu Pro Phe Arg Asp Pro Asn Ser Glu Glu Asn Ser Asn
                305                 310                 315

Asp Ile Ala Leu Val His Leu Ser Ser Pro Leu Pro Leu Thr Glu
                320                 325                 330
```

-continued

```
Tyr Ile Gln Pro Val Cys Leu Pro Ala Ala Gly Gln Ala Leu Val
                335                 340                 345

Asp Gly Lys Ile Cys Thr Val Thr Gly Trp Gly Asn Thr Gln Tyr
                350                 355                 360

Tyr Gly Gln Gln Ala Gly Val Leu Gln Glu Ala Arg Val Pro Ile
                365                 370                 375

Ile Ser Asn Asp Val Cys Asn Gly Ala Asp Phe Tyr Gly Asn Gln
                380                 385                 390

Ile Lys Pro Lys Met Phe Cys Ala Gly Tyr Pro Glu Gly Gly Ile
                395                 400                 405

Asp Ala Cys Gln Gly Asp Ser Gly Gly Pro Phe Val Cys Glu Asp
                410                 415                 420

Ser Ile Ser Arg Thr Pro Arg Trp Arg Leu Cys Gly Ile Val Ser
                425                 430                 435

Trp Gly Thr Gly Cys Ala Leu Ala Gln Lys Pro Gly Val Tyr Thr
                440                 445                 450

Lys Val Ser Asp Phe Arg Glu Trp Ile Phe Gln Ala Ile Lys Thr
                455                 460                 465

His Ser Glu Ala Ser Gly Met Val Thr Gln Leu
                470                 475
```